US005694211A

United States Patent [19]

Ohsuka et al.

[11] Patent Number: 5,694,211
[45] Date of Patent: Dec. 2, 1997

[54] LIGHT MEASURING APPARATUS FOR QUANTIZING PHOTON

[75] Inventors: Shinji Ohsuka; Hisayoshi Takamoto, both of Himakita, Japan

[73] Assignee: Laboratory of Molecular Biophotonics, Shizuoka, Japan

[21] Appl. No.: 767,933

[22] Filed: Dec. 17, 1996

[30] Foreign Application Priority Data

Dec. 19, 1995 [JP] Japan .................................. 7-330482
Sep. 24, 1996 [JP] Japan .................................. 8-251787

[51] Int. Cl.$^6$ ..................................................... G01J 1/42
[52] U.S. Cl. ........................... 356/218; 356/226; 250/368
[58] Field of Search ........................ 356/213, 226, 356/215, 216, 218; 250/214 A, 214 R, 366, 367, 368; 307/311

[56] References Cited

U.S. PATENT DOCUMENTS 4,498,012  2/1985  Duda ..................................... 250/578
4,931,647  6/1990  Hiruma et al. .
5,115,667  5/1992  Baret ..................................... 356/226

FOREIGN PATENT DOCUMENTS 6075387  9/1994  Japan .
7167709  7/1995  Japan .
1097558  1/1968  United Kingdom .
1596289  8/1981  United Kingdom .
2273771  6/1994  United Kingdom .

OTHER PUBLICATIONS

Bass et al., "Handbook of Optics", vol. II, pp. 20.5–20.12, Jan. 1995.
Dr. R. W. Engstrom, "Photomultiplier Handbook", (Jan. 1980), pp. 160–176.
Birch et al., "Time–Domain Fluorescence Spectroscopy Using Time–Correlated . . . ", Dept. of Physics & Applied Physics, pp. 1–15, (Jan. 1991).
Cushman et al., "A Multichannel Avalanche Photodiode Phototube for . . . ", Nuclear Physics B (Proc. Suppl.) 44 (1995) pp. 35–39.
Suyama et al., "Fundamental Investigation of Vacuum . . . ", IEEE Trans. on Nuclear Sci., vol. 41, No. 4, Aug. 1994, pp. 719–723.
S. J. Fagen, "Vacuum avalanche photodiodes can count single photons", Laser Focus World, Nov. 1993, pp 125–132.
Cushman et al., "A photomultiplier tube incorporating an avalanche photodiode", Nuclear Instruments and Methods in Physics Research A 333 (1993), pp. 381–390.
Basa et al., "Test results of the first Proximity Focused Hybrid Photodiode . . . ", Nuclear Instruments and Method in Physics Research A 330 (1993), pp. 93–99.
Johansen et al., "Operational characteristics of an electron–bombarded silicon–diode photomultiplier tube", Nuclear Instruments and Methods of Physics Research A326 (1993), pp. 295–298.
DeSalvo et al., "First results on the hydrid photodiode tube", Nuclear Instruments and Methods in Physics Research A 315 (1992) pp. 375–384.

*Primary Examiner*—Hoa Q. Pham
*Attorney, Agent, or Firm*—Leydig, Voit & Mayer, Ltd.

[57] ABSTRACT

When incident light is incident to a photodetector, photoelectrons are emitted and multiplied in each of incident zones whereby a plurality of current signals are output. These current signals each are processed to estimate a distribution or a mean value of numbers of photoelectrons generated in each incident zone. Then estimated based on the estimate values of respective incident zones is the number of photoelectrons emitted from the entire photoelectric conversion surface. In this way the intensity of incident light is measured with accuracy.

29 Claims, 24 Drawing Sheets

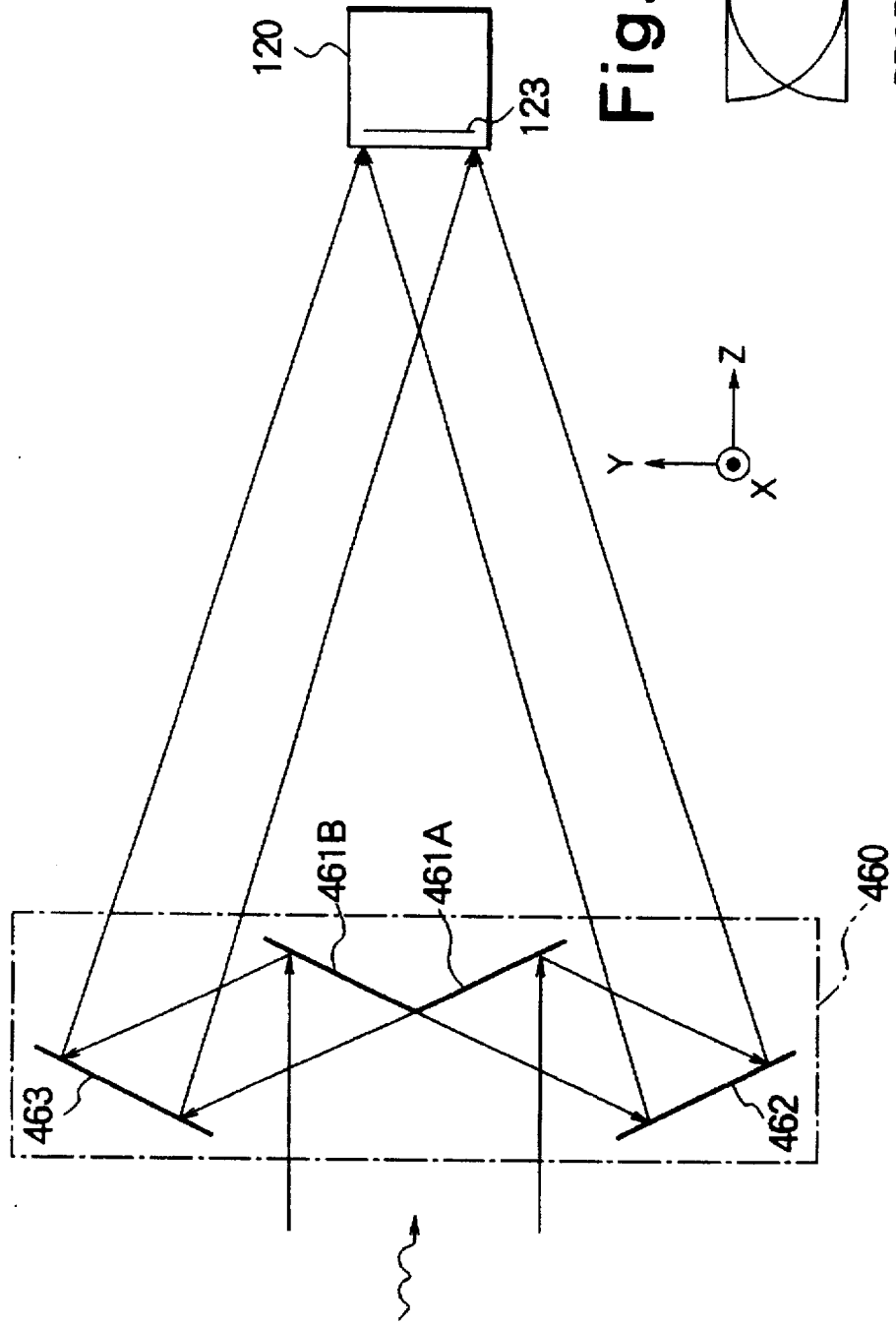
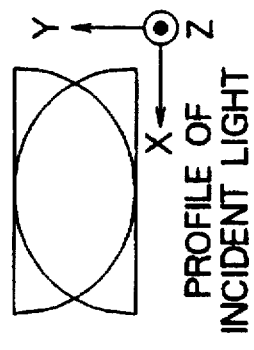

LIGHT MEASURING APPARATUS FOR QUANTIZING PHOTON

BACKGROUND OF THE INVENTION

1. Field of the Invention

The present invention relates to a light measuring apparatus for counting the number of photons of incident light, and more particularly, to a light measuring apparatus for quantizing photon used, for example in the field of biochemistry or the like, for counting the number of photons of fluorescence radiated from a sample excited by a pulsed light source and quantitatively measuring the number of fluorescent molecules in the sample.

2. Related Background Art

For quantitatively measuring an amount of a fluorescent substance (or fluorescent molecules) in a sample, the sample is irradiated by excitation light and the intensity of fluorescence occurring from the fluorescent substance is measured. A typical device having been used heretofore for such measurement is a fluorophotometer, for example, using a xenon lamp as a light source and a photomultiplier tube as a fluorescence detector. In general, the xenon lamp is lighted not pulsatively but continuously and the photomultiplier tube receives the fluorescence generated by the fluorescent substance to continuously output an output current according to the intensity of the fluorescence. The fluorescence intensity is measured in this manner and the amount of the fluorescent material is quantitatively measured based on the value of the output current from the photomultiplier tube.

However, in the cases where the amount of the fluorescent substance in the sample is very small and the fluorescence intensity, depending upon the intensity of the excitation light from the xenon lamp, is below the detection limit, the above fluorophotometer cannot be used. In such cases, the amount of the fluorescent substance is quantitatively determined by the photon counting method for measuring the intensity of fluorescence based on a count value of output pulses from the photomultiplier tube. Also, a laser light source is used as an excitation light source for generating the excitation light with high intensity. Further, a pulsed laser light source for outputting pulsed light is used for removing dark noise of the photomultiplier tube while obtaining the high intensity of excitation light. Also in such cases, similarly as in the above example, the photomultiplier tube measures the intensity of fluorescence generated by the fluorescent substance in the sample excited by laser light and the amount of the fluorescent substance is quantitatively measured based on the count value of output pulses from the photomultiplier tube.

SUMMARY OF THE INVENTION

An object of the present invention is to provide a light measuring apparatus that can measure the intensity of measurement-object light or a spectrum thereof even if a great number of photoelectrons are emitted with incidence of the measurement-object light to a photoelectric conversion surface of photodetector or even if a peak intensity difference is large upon measurement of the spectrum of measurement-object light.

A light measuring apparatus of the present invention comprises: (a) photodetection means having a photoelectric conversion surface for emitting photoelectrons in a number according to a photodetection number distribution depending upon a number of photons of incident light, and a plurality of electron multiplier portions provided corresponding to a plurality of zones of the photoelectric conversion surface, each electron multiplier portion multiplying photoelectrons emitted from an associated zone of the photoelectric conversion surface to output a current signal as to the associated zone; (b) collecting means for collecting photoelectron occurrence events in the respective zones of the photoelectric conversion surface in a gate period, based on current signals output from the respective electron multiplier portions; and (c) estimating means for estimating a distribution of numbers of photoelectrons emitted with incidence of measurement-object light in each zone of the photoelectric conversion surface in the gate period, based on collection results by the event collecting means, and thereby obtaining an intensity of the measurement-object light.

Here, the photodetection means may be arranged (i) to comprise a photodetection means which comprises a photoelectric conversion surface for emitting photoelectrons in a number according to a photon number distribution of incident light in each of plural zones; a plurality of electron multiplier portions, each multiplying photoelectrons emitted from an associated zone of the photoelectric conversion surface to output a current signal as to the associated zone; and a vacuum vessel having a transmissive window for letting the incident light pass and enclosing the photoelectric conversion surface and the electron multiplier portions therein, or (ii) to have an array of photodetection means each of which has a photocathode corresponding to one of the plural zones of the photoelectric conversion surface, for emitting photoelectrons in the number according to the distribution of photon numbers of the incident light, an electron multiplier portion for multiplying each of photoelectrons emitted from the photocathode to output electrons as a current signal, and a vacuum vessel having a transmissive window for letting the incident light pass and enclosing the photocathode and electron multiplier portion therein.

In this light measuring apparatus, if the number of photoelectrons emitted is large when the incident light is incident to the photoelectric conversion surface, the entrance zone is enlarged whereby the incident light is received by a plurality of zones of the photoelectric conversion surface.

Therefore, the number of photoelectrons emitted is large for the whole of the photoelectric conversion surface, but, as to each zone, the number of photoelectrons emitted is small.

Then the photoelectrons emitted from each zone of the photoelectric conversion surface are multiplied by the electron multiplier portion provided for each zone, and are output as a photodetection current signal of each zone from the photodetection means.

The current signals output from the respective electron multiplier portions are supplied to the collecting means, and the collecting means collects the photoelectron occurrence events for every zone of the photoelectric conversion surface in the gate period. Based on the collection results thus obtained by the event collecting means, the estimating means estimates a distribution of numbers of photoelectrons emitted with incidence of the measurement-object light for each zone of the photoelectric conversion surface in the gate period, thus obtaining the intensity of the measurement-object light.

According to the knowledge of the inventor obtained as the results of research, for example, the number of photoelectrons emitted from the photoelectric conversion surface of the photomultiplier tube per irradiation of sample with a pulse of laser light is dependent on the photoelectron number distribution according to the intensity of incident light. Let p(1) be a probability that the number of photoelectrons emitted in accordance with this photoelectron number distribution is 1 and p(x≥2) be a probability that the number is 2 or more. The photoelectron number distribution in the photoelectric conversion surface is assumed to be a Poisson distribution. In this case, for example, if the mean value λ of numbers of photoelectrons emitted from the photoelectric conversion surface when the photomultiplier tube receives the fluorescence generated from the fluorescent substance excited by a pulse of pulsed laser light is over 0.1, p(x≥2)/p(1) becomes 5 or more %. Since greater p(x≥2)/p(1) increases the number of photoelectrons not counted and makes deviation larger from the proportional relation of the intensity of fluorescence incident to the photomultiplier tube with respect to the count value of output pulses from the photomultiplier tube, determination of quantity of the fluorescent substance from the count value of output pulses from the photomultiplier tube will cause a great error.

For example, there are some cases where intensity peaks appear at many wavelengths in measurement of spectrum by a spectroscope, and in such cases the following problem will arise in use of the conventional light measuring apparatus. Namely, in such cases, the intensity of the overall wavelength band of the measurement-object light is adjusted so that measurement by the photon counting method can be performed ideally for the highest peak intensity. However, if there are great differences of peak intensity between peaks, the maximum peak intensity will be measured with accuracy, but upon measurement of small peak intensities small count values will result in relatively increasing the quantum noise so as to degrade the measurement accuracy. On the other hand, when the small peak intensities are attempted to be measured with accuracy, the intensity of the whole of the measurement-object light needs to be set high, which will cause failure in counting of photoelectrons upon measurement of large peak intensity, so as to degrade the measurement accuracy.

In the case of the light measuring apparatus of the present invention, even if the number of photoelectrons emitted is large from the entire photoelectric conversion surface with incidence of incident light thereto, the number of photoelectrons emitted from each zone is small, and the apparatus is arranged to estimate a distribution of numbers of photoelectrons emitted with incidence of measurement-object light for each zone of the photoelectric conversion surface, whereby the intensity of the measurement-object light can be obtained with accuracy.

In a first aspect of the light measuring apparatus of the present invention, the collecting means comprises: (i) integrating means provided for each of the electron multiplier portions, each integrating means integrating the current signal output from each electron multiplier portion to convert the current signal to a voltage signal and outputting the voltage signal as a pulse height value of one event; and (ii) first generating means for collecting pulse height values for every event as to each electron multiplier portion and generating pulse height distributions (N$_j$(h); h is pulse height values) of number of event against pulse height value; and the estimating means comprises: (i) second generating means for generating a pulse height distribution of single photoelectron events (p$_1$(h)), based on the pulse height distribution (N$_{1,j}$(h)) generated by the first generating means, for each electron multiplier portion in the case of setting in a collection mode of single photoelectron events in each of which a number of photoelectrons emitted in the photodetection means is substantially at most one; (ii) third generating means for recursively calculating values as defined below, for each electron multiplier portion, based on the pulse height distribution of single photoelectron events (p$_{1,j}$(h)), $$p_{k,j}(h) = \int_0^h (p_{k-1,j}(l) - p_{1,j}(h-l))dl \quad (1)$$

and thereby generating pulse height distributions of k-photoelectron events (p$_{k,j}$(h)) in each of which a number of photoelectrons emitted from the photodetection means is k(2≤k≤k$_{MAX}$), for each zone of the photoelectric conversion surface; and (iii) photoelectron number distribution estimating means for estimating the photoelectron number distribution for a case wherein the measurement-object light is incident to the photodetection means, based on pulse height distributions (N$_j$(h)) generated by the first generating means when the measurement-object light is incident to the photodetection means in the case of setting in a normal measurement mode, the pulse height distributions of single photoelectron events already obtained (p$_{1,j}$(h)), and the pulse height distributions of k-photoelectron events already obtained (p$_{k,j}$(h)), thereby obtaining the intensity of the measurement-object light.

Prior to the normal light measurement, this light measuring apparatus collects single photoelectron events in each of which the number of photoelectrons emitted from each zone of the photoelectric conversion surface is at most one. It is theoretically impossible to generate only single photoelectron events, but it is possible to make a probability of occurrence of single photoelectron events overwhelmingly dominant by setting the intensity of the light incident to each zone of the photoelectric conversion surface very weak.

First, when the light is incident to each zone of the photoelectric conversion surface in the state in which the very weak light is incident to the photodetection means, at most one photoelectron is emitted in each zone of the photoelectric conversion surface in most cases. Then the photoelectrons emitted are multiplied in the electron multiplier portion provided corresponding to each zone, whereby a photodetection current signal is output as to each zone of the photoelectric conversion surface. Each of these current signals is integrated over a predetermined time by the integrating means to become a voltage signal of one event. Since the number of photoelectrons emitted from each zone of the photoelectric conversion surface in accordance with one event (i.e., during the predetermined period of time) is at most one in the most cases, as described above, this voltage signal becomes a value according to a single photoelectron event in the most cases. The voltage value of the voltage signal of each event is collected as a pulse height value of each event by the first generating means. The first generating means generates the pulse height distributions N$_{1,j}$(h) based on the pulse height values collected.

Next, the second generating means takes in the pulse height distributions N$_{1,j}$(h) generated by the first generating means and eliminates the noise in the low-pulse-height portion and zero-photoelectron events, based on the pulse height distributions N$_{1,j}$(h), thereby generating the pulse height distributions p$_{1,j}$(h) of single photoelectron events in correspondence to the respective zones of the photoelectric conversion surface.

Then the third generating means takes in the pulse height distributions p$_{1,j}$(h) of single photoelectron events generated by the second generating means, and recursively calculates the following values, based on the pulse height distributions p$_{1,j}$(h), $$p_{k,j}(h) = \int_0^h (p_{k-1,j}(l) - p_{1,j}(h-l))dl \quad (1)$$

and thereby generating the pulse height distributions of k-photoelectron events $p_{k,j}(h)$ in each of which the number of photoelectrons emitted from the photodetection means is $k(2 \leq k \leq k_{MAX})$, in correspondence to the respective zones of the photoelectric conversion surface.

After obtaining the pulse height distributions $p_{i,j}(h)$ of events in each of which the number of photoelectrons emitted from the photodetection means is $i(1 \leq i \leq k_{MAX})$ for the respective zones of the photoelectric conversion surface in this way, normal measurement of measurement-object light is carried out.

For normal measurement of the measurement-object light, first, the measurement-object light is made incident to the photoelectric conversion surface of the photodetection means to emit photoelectrons. The photoelectrons thus generated are multiplied in the electron multiplier portions, and the photodetection current signals $I_j$ are output as to the respective zones of the photoelectric conversion surface. These current signals $I_j$ each are integrated over the predetermined time by the integrating means to become voltage signals of one event. The first generating means collects the voltage values of the voltage signals of each event as pulse height values of each event. The first generating means generates the pulse height distributions $N_j(h)$ based on the pulse height values collected.

Next, the estimating means collects the pulse height distributions $N_j(h)$ generated by the first generating means and the pulse height distributions $p_{i,j}(h)$ generated by the third generating means. Then, based on the pulse height distributions $N_j(h)$ and pulse height distributions $p_{i,j}(h)$, the estimating means estimates the photoelectron number distribution for each zone of the photoelectric conversion surface in one event when the measurement-object light is incident to the photodetection means.

Then the intensity of the measurement-object light is obtained from the photoelectron number distributions in one event estimated upon incidence of the measurement-object light.

As described above, this apparatus is arranged to preliminarily prepare for occurrence of k-photoelectron events where plural photoelectrons occur in each zone of the photoelectric conversion surface and to estimate the pulse height distributions $p_{k,j}(h)$ of k-photoelectron events with statistic reliability, based on the pulse height distributions $p_{1,j}(h)$ of single photoelectron events being a kind of calibration data, obtained by measurement. Therefore, even if the number of photoelectrons occurring in each event is unknown and even if the probability of occurrence of plural photoelectrons in each event is high, the apparatus can estimate the photoelectron number distribution of photoelectrons occurring in each zone of the photoelectric conversion surface of the photodetection means upon incidence of the measurement-object light from the pulse height distributions $N_j(h)$ with reference to the pulse height distributions $p_{i,j}(h)$ ($1 \leq i \leq k_{MAX}$), whereby the apparatus can estimate the photoelectron number distribution of photoelectrons occurring in each zone of the photoelectric conversion surface upon incidence of the measurement-object light with accuracy, and can in turn obtain the intensity of the measurement-object light with accuracy.

In the apparatus of the first aspect of the present invention, each of the electron multiplier portions of the photodetection means may be preferably constructed as employing an avalanche photodiode, between an anode and a cathode of which a reverse bias voltage is applied and a portion of which opposed to the photoelectric conversion surface is set at a higher potential than a potential of the photoelectric conversion surface, for avalanche-multiplying electron-hole pairs generated with incidence of the photoelectrons and outputting the current signal according to a number of electron-hole pairs thus avalanche-multiplied.

Since the photodetection means of this type has the high resolution of pulse height value against photoelectron number and can clearly identify peaks according to respective k-photoelectron events in each of which the number of photoelectrons emitted from each zone of the photoelectric conversion surface with incidence of light is k, in the pulse height distribution of current signals output from the respective electron multiplier portions, it can accurately measure the photoelectron distribution in each zone of the photoelectric conversion surface according to the intensity of incident light, and the intensity of the incident light.

In this light measuring apparatus, the first generating means may be arranged to comprise: (i) an analog-to-digital converter for receiving the voltage signal every event, converting the voltage signal to a digital value, and outputting the digital signal as a pulse height value; and (ii) event counting means for counting and storing a number of events occurring, for each digital value output from the analog-to-digital converter, whereby pulse heights h can be handled not as a continuous analog value, but as discrete digital values.

In this case, the third generating means calculates the values defined below to obtain pulse height distributions of k-photoelectron events $(p_{k,j}(h))$, $$p_{k,j}(h) = \sum_{l=0}^{h} (p_{k-1,j}(l) - p_{1,j}(h-l)) \quad (2)$$

Since the digital values are starting values for the calculation arithmetic in this way, a digital computer having the calculation programs can be suitably used as a means for executing the calculation.

In the apparatus of the first aspect of the present invention, the estimating means can estimate the photoelectron number distribution by the maximum likelihood method. Also, the estimating means can estimate the photoelectron number distribution under such an assumption that the photoelectron number distribution is a Poisson distribution. In either case, the photoelectron number distribution according to the intensity of incident light, and the intensity of the incident light can be measured with accuracy.

When the pulse height values h and pulse height distributions $p_i(h)$, N(h) are digital values, a digital computer may be suitably used for estimation of the photoelectron number distribution in each zone of the photoelectric conversion surface.

Occurrence of single photoelectron events can be implemented by employing a calibration sample emitting very weak light, instead of the measurement object.

It is also possible to use the measurement object as it is and to reduce the light before incidence to the photodetection means so that most occurrence events in the photodetection means are single photoelectron events. According to this method, the light measuring apparatus of the present invention may be arranged to further comprise light reducing means such as a light reducing filter for reducing the quantity of light incident to the photodetection means in the case of setting in the collection mode of single photoelectron events.

The light measuring apparatus of the first aspect of the present invention can be applied to measurement of fluorescence occurring in the measurement object by irradiation of the measurement object with excitation light. For such measurement of fluorescence, the apparatus is preferably arranged to further comprise (i) a pulsed light source for outputting pulsed light for irradiating a measurement object and also outputting a generation timing signal of the pulsed light; (ii) operation timing signal generating means for generating an integration instruction signal and a collection instruction signal from the generation timing signal of the pulsed light and for sending the integration instruction signal to the integrating means and the collection instruction signal to the first generating means; and (iii) a counter for counting a number of generation times of the pulsed light from the generation timing signal of the pulsed light.

Occurrence of single photoelectron events upon measurement of fluorescence can be realized by irradiating a calibration sample containing a very fine, known amount of fluorescent substance with excitation light, in place of the measurement object.

It is also possible to use the measurement object as it is and to reduce the fluorescence before incidence to the photodetection means so that most occurrence events in the photodetection means are single photoelectron events. According to this method, the light measuring apparatus of the present invention may be arranged to further comprise the light reducing means such as a light reducing filter for reducing the quantity of light incident to the photodetection means in the case of setting in the collection mode of single photoelectron events.

It is also possible to use the measurement object as it is and to reduce the excitation light before irradiation of the measurement object so that most occurrence events in the photodetection means are single photoelectron events. According to this method, the light measuring apparatus of the present invention may be arranged to further comprise the light reducing means such as a light reducing filter for reducing the intensity of the excitation light before irradiation of the measurement object with the excitation light in the case of setting in the collection mode of single photoelectron events.

The light measuring apparatus of the first aspect of the present invention is preferably arranged to further comprise measurement control means for giving an instruction of activation of the second generating means in the case of setting in the collection mode of single photoelectron events and giving an instruction of activation of the photoelectron number distribution estimating means in the case of setting in the normal measurement mode.

In this case, an operator of the light measuring apparatus needs only to notify the measurement control unit of either collection of single photoelectron events or collection of events with the normal measurement-object light without a need for performing collection of single photoelectron events or collection of events with the normal measurement-object light by individually manipulating the second generating means and third generating means, which makes the measurement easy.

For example, for measuring spontaneously emitted light from the measurement object or measuring fluorescence occurring upon continuous irradiation of excitation light, the measurement control means can send an integration instruction signal to the integrating means and can send a collection instruction signal to the first generating means.

When the apparatus is arranged to comprise a measurement control unit, the measurement control unit, receiving a notification of either collection of single photoelectron events or collection of events with the normal measurement-object light sent to the measurement control unit, issues a single photoelectron event instruction signal upon occurrence of single photoelectron events by the light reducing filter, and the apparatus can be arranged to further comprise carrying means for locating the light reducing filter in an optical path of the measurement-object light or the excitation light when the single photoelectron event instruction signal is significant, but removing the light reducing filter from the optical path of the measurement-object light or the excitation light when the single photoelectron event instruction signal is non-significant.

In the light measuring apparatus of the second aspect of the present invention, the collecting means comprises: (i) a discriminator for receiving a current signal output from each electron multiplier portion in accordance with each electron multiplier portion and outputting a discrimination signal of photoelectron occurrence when a current value is at least a predetermined value, in the gate period; and (ii) recording means for recording event occurrence for each zone of the photoelectric conversion surface as regarding as an event a case wherein the discrimination signal becomes significant one or more times within the gate period; and the estimating means estimates a mean value of photoelectrons emitted from each zone of the photoelectric conversion surface in the gate period, based on information of the event occurrence recorded in the recording means, thereby obtaining the intensity of the measurement-object light.

In this light measuring apparatus, first, the measurement-object light is made incident to the photoelectric conversion surface of the photodetection means, thereby emitting photoelectrons. The photoelectrons thus generated are multiplied by the electron multiplier portions, and the photodetection current signal $I_j$ of each zone of the photoelectric conversion surface is output.

Each current signal $I_j$ is supplied to the discriminator, and the discriminator outputs a discrimination signal of occurrence of photoelectron if the current value is at least the predetermined value, within the gate period. Then the recording means records event occurrence for each zone of the photoelectric conversion surface as regarding as an event a case wherein the discrimination signal becomes significant one or more times in the gate period.

Next, the estimating means estimates the mean value of photoelectrons emitted from each zone of the photoelectric conversion surface in the gate period, based on information of event occurrence recorded in the recording means, thereby obtaining the intensity of the measurement-object light.

As a result, even if the intensity of the measurement-object light is so high as to cause the photoelectric conversion surface to emit many photoelectrons, the measurement-object light is separated into plural segmental light and the mean value of photoelectrons emitted from each zone of the photoelectric conversion surface can be estimated from occurrence conditions of event based on the relatively small number of photoelectrons emitted with incidence of each segmental light, whereby the intensity of the measurement-object light can be measured with accuracy.

In the apparatus of the second aspect of the present invention, the estimating means can estimate the photoelectron number distribution in each zone of the photoelectric conversion surface by the maximum likelihood method. Also, the photoelectron number distribution can be estimated under such an assumption that the photoelectron number distribution is a Poisson distribution. In either case, the photoelectron number distribution according to the intensity of the incident light, and the intensity of the incident light can be measured with accuracy.

The apparatus of the second aspect of the present invention can be applied to measurement of fluorescence occurring in the measured object by irradiation of the measurement object with excitation light. For such fluorescence measurement, the apparatus is preferably arranged to further comprise (i) a pulsed light source for outputting pulsed light for irradiating a measurement object and also outputting a generation timing signal of the pulsed light; (ii) operation timing signal generating means for generating the integration instruction signal and the collection instruction signal from the generation timing signal of the pulsed light and for sending the integration instruction signal to the integrating means and the collection instruction signal to the first generating means; and (iii) a counter for counting a number of generation times of the pulsed light from the generation timing signal of the pulsed light.

The apparatus of the second aspect of the present invention is preferably arranged to further comprise a homogenizing optical system for homogenizing the intensity distribution on the photoelectric conversion surface, of the measurement-object light incident to the photoelectric conversion surface.

In this case, occurrence of photoelectrons in each zone of the photoelectric conversion surface is homogenized and the measurement accuracy is prevented from being degraded only in a specific zone of the photoelectric conversion surface, whereby measurement can be performed with accuracy even if the intensity of the measurement-object light is high.

The apparatus of the second aspect of the present invention is preferably arranged to further comprise a dividing optical system for receiving the measurement-object light, dividing the measurement-object light, and making each divided light incident to a corresponding zone of the photoelectric conversion surface.

In this case, since the measurement-object light is incident to each zone of the photoelectric conversion surface, the measurement-object light can be prevented from being concentrated only in a specific zone of the photoelectric conversion surface, whereby measurement can be performed with accuracy even if the intensity of the measurement-object light is high.

The apparatus of the first or second aspect of the present invention may be arranged to further comprise a spectroscope for separating the incident light and emitting light of a wavelength selected toward the photodetection means, whereby measurement of a spectrum of the measurement-object light can be carried out with accuracy.

The present invention will become more fully understood from the detailed description given hereinbelow and the accompanying drawings which are given by way of illustration only, and thus are not to be considered as limiting the present invention.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

FIG. 22 and FIG. 23 are explanatory drawings of homogenizing optical system 460;

DESCRIPTION OF THE PREFERRED EMBODIMENTS

Figure 1:
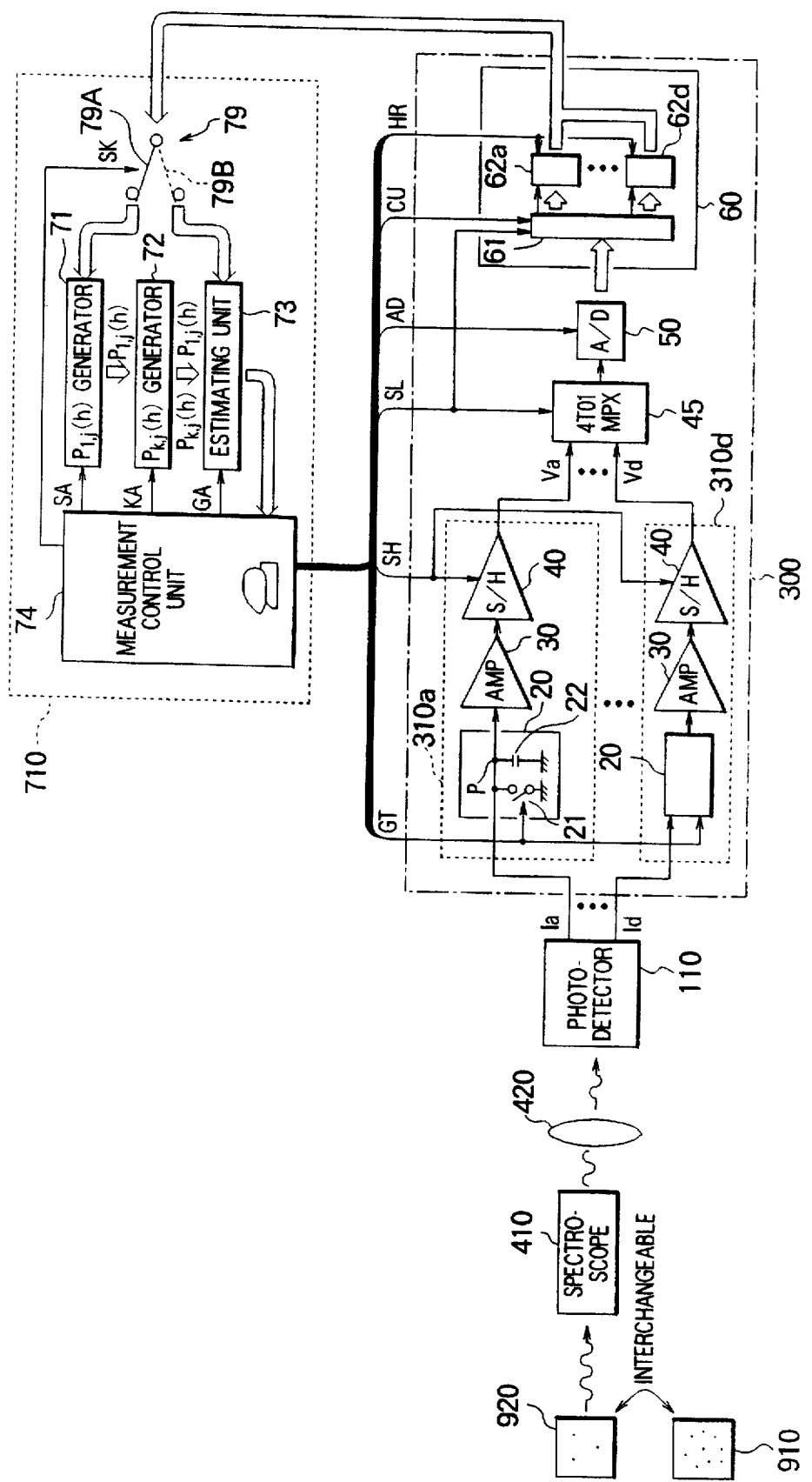
FIG. 1 is a structural drawing of a light measuring apparatus according to Embodiment 1 of the present invention.

The embodiments of the present invention will be described with reference to the accompanying drawings. In the description of the drawings same elements will be denoted by same reference numerals and redundant description will be omitted.

(Embodiment 1)

FIG. 1 is a structural drawing of the light measuring apparatus according to Embodiment 1 of the present invention. As shown in FIG. 1, the apparatus of the present embodiment comprises (a) a spectroscope 410 for receiving spontaneous emission light from a measured object 910 or from a calibration sample 920 to separate the light and emitting light of wavelengths being a measurement object, (b) a photodetector 110 for receiving the measurement-object light emitted from the spectroscope 410 and coming through an optical system 420, emitting photoelectrons in the number according to a distribution of photoelectron numbers depending upon the number of photons of incident light, multiplying photoelectrons emitted from each of plural zones in a photoelectric conversion surface emitting the photoelectrons, and outputting pulse current signals $I_j$ (j=a to d) of every zone of the photoelectric conversion surface, (c) a collector 300 for collecting pulse height values of the pulse current signals $I_j$ for every one event and generating pulse height distributions of event number against pulse height value ($N_j$(h); h is pulse height values), and (d) a processing section 710 for collecting and processing the pulse height distributions ($N_j$(h)) generated by the collector 300 and outputting operation timing signals (GT, SH, SL, AD, CU, HR) to the collector 300.

Figure 2:
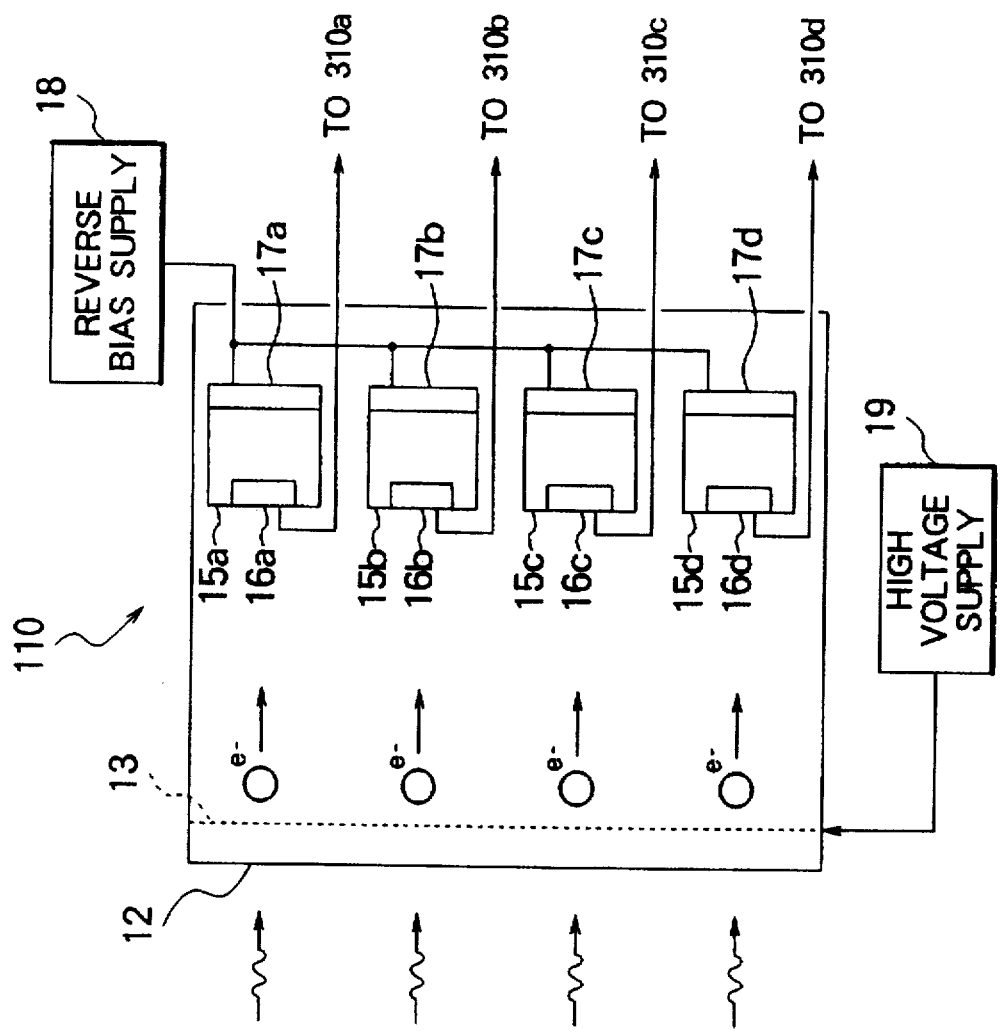
FIG. 2 is a structural drawing of photodetector 110 utilizing avalanche photodiodes (APDs)

FIG. 2 is a structural drawing of the photodetector 110. As shown in FIG. 2, the photodetector 110, receiving incident light, is arranged so that when the incident light is incident to the photoelectric conversion surface 13, it emits photoelectrons in the number according to a distribution thereof depending upon the quantity of the incident light and so that a predetermined number of multiplier units are arranged in an array as each facing the photoelectric conversion surface 13 so as to multiply photoelectrons incident thereto and output a current signal. The multiplier units are preferably avalanche photodiodes (hereinafter, APDs), for example.

This photodetector 110 is arranged in such a manner that an entrance window 12 is formed in a part of a vacuum vessel 11 the inside of which is kept in a vacuum and that the incident light passes through the entrance window 12 to reach the photoelectric conversion surface 13. APDs 15a to 15d are arranged in a one-dimensional or two-dimensional array as facing the photoelectric conversion surface 13, and this array is nearly parallel to the photoelectric conversion surface 13. In the present embodiment, four APDs are arranged in a one-dimensional array. Since a high-voltage supply 19 applies a high voltage, −10 kV to −15 kV for example, to the photoelectric conversion surface 13 with respect to the arrayedAPDs 15a to 15d, the photoelectric conversion surface 13, when the incident light is incident there number according electrons in the number according to the distribution thereof depending upon the quantity of the incident light. Then the photoelectrons are accelerated by an electric field between the photoelectric conversion surface 13 and the APDs 15a to 15d to enter either one of the APDs 15a to 15d.

Figure 3:
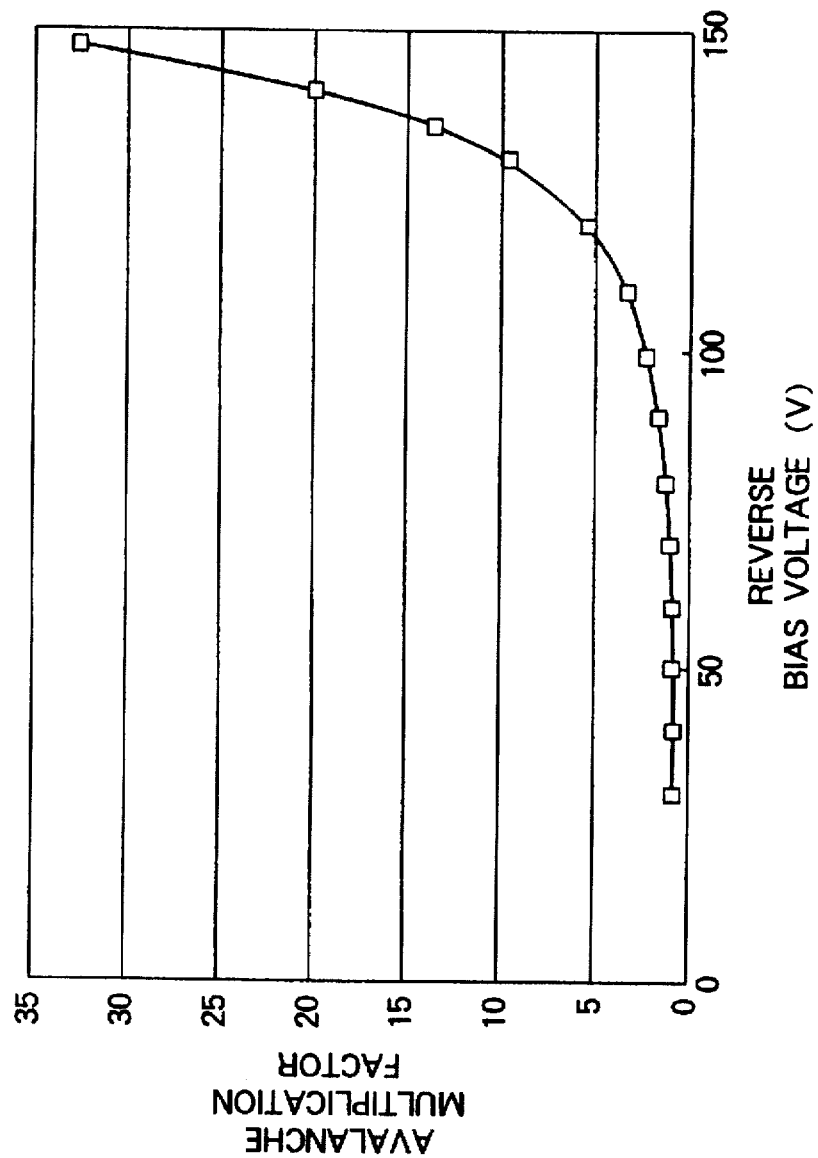
FIG. 3 is a graph to show the relationship between reverse bias voltage and avalanche multiplication factor in the APDs.

The APD 15a among them will be explained. A reverse bias voltage (+145 V, for example) is applied between the anode 16a and the cathode 17a thereof by a reverse bias supply 18 and the potential of the anode 16a facing the photoelectric conversion surface 13 is set higher than that of the photoelectric conversion surface 13. When the photoelectrons are emitted from a zone of the photoelectric conversion surface 13 facing this APD 15a, they collide with the anode 16a to generate a pair of electron and hole per energy 3.6 eV which the photoelectrons have lost for ionization in the APD 15a. Then the electron-hole pairs are avalanche-multiplied according to the avalanche multiplication factors having the relation shown in FIG. 3 against the reverse bias voltage, in the APD 15a to be output as an electric current signal between the anode terminal and the cathode terminal. However, the energy lost in the APD 15a by the photoelectrons is not constant, but is according to a certain distribution. Further, the multiplication factors of APD 15a are not constant, either, but are according to a certain multiplication factor distribution. Therefore, magnitudes of current signals output upon incidence of single photoelectron are also distributed in a certain distribution.

Accordingly, when the photodetector 110 detects light of constant intensity many times, a distribution of numbers of photoelectrons emitted from the photoelectric conversion surface 13 and entering the APD 15a (a photoelectron number distribution) becomes a distribution spread around a certain mean value according to the light intensity, so that current signals output from the photodetector 110 have a distribution further spread in accordance with a distribution of numbers of electron-hole pairs output from the APD 15a with incidence of single photoelectron.

The APDs 15b to 15d are also constructed in the same structure as the above APD 15a. It is, however, noted that potential differences between each anode 16a to 16d and the photoelectric conversion surface 13 may be constant or different from each other. Also, the reverse bias voltages applied to the APDs 15a to 15d may be constant or different from each other. In the case of the APDs 15a to 15d each having same characteristics, it is convenient in respect of subsequent processing to apply a same voltage thereto to secure a same multiplication factor. On the other hand, if the APDs 15a to 15d have characteristics different from each other, it is preferable to apply appropriate voltages to the respective APDs in order to secure a same multiplication factor.

The APDs 15a to 15d each may be constructed as mutually independent elements or may be integrated on a substrate. In the latter case, handling becomes easy, because many APDs with same characteristics are precisely arrayed at predetermined positions.

The collector 300 comprises (i) signal processing sections $310_j$, each receiving the pulse current signal $I_j$ (j=a to d), converting it into a voltage signal $V_j$, and sampling it, (ii) a selector circuit 45 for receiving the voltage signals $V_j$ and selecting one of the voltage signals $V_a$ to $V_d$ in accordance with a selection signal SL to output it, (iii) an analog-to-digital converter (AD converter) 50 for receiving the voltage signal as an analog signal output from the selector circuit 45 and converting it to a digital signal having a digital value (i.e., a pulse height value) according to a voltage value, in accordance with an AD conversion instruction signal AD, and (iv) a multi-channel histogramming memory 60 for receiving the digital signal output from the AD converter 50 and cumulatively adding a predetermined value (1, for example) to an address according to the pulse height value for each photoelectron generating zone (13a to 13d) in response to selection signal SL and addition signal CU.

Each of the signal processing sections $310_j$ comprises (i) an integrator 20 for integrating the pulse current signal $I_j$ in response to a gate signal GT to convert it to a voltage signal and output it as a pulse height value depending upon a photoelectron generating zone, in one event, (ii) an amplifier 30 for receiving the voltage signal output from the integrator 20 and amplifying and outputting it, and (iii) a sample holder 40 for sampling or holding the voltage signal output from the amplifier 30 in accordance with a sample instruction signal.

The multi-channel histogramming memory 60 comprises (i) a demultiplexer circuit 61 for receiving the digital signal output from the AD converter 50, selection signal SL, and addition signal CU and outputting the digital signal and addition signal CU to a line according to the selection signal SL, and (ii) histogramming memory units $62_a$ to $62_d$ for cumulatively adding the predetermined value to an address according to a pulse height value. The contents of the histogramming memory units $62_a$ to $62_d$ all are reset to 0 in accordance with an instruction of memory reset signal HR.

The processing section 710 comprises (i) a generator 71 activated in accordance to an activation instruction signal SA to generate pulse height distributions of single photoelectron events ($p_{1,j}(h)$) in the respective zones $13_j$ of the photoelectric conversion surface, based on pulse height distributions ($N_{1,j}(h)$) generated by the collector 300, (ii) a generator 72 for recursively calculating Eq. 4 defined below based on the pulse height distributions of single photoelectron events ($p_{1,j}(h)$), $$p_{k,j}(h) = \sum_{l=0}^{h} (p_{k-1,j}(l) - p_{1,j}(h-l)) \qquad (2)$$

thereby obtaining pulse height distributions of k-photoelectron events ($p_{k,j}(h)$), in each of which the number of photoelectrons emitted in the photodetector 110 is $k(2 \leq k \leq k_{MAX})$, for each zone $13_j$ of the photoelectric conversion surface, (iii) an estimating unit 73 for estimating photoelectron number distributions for every zone $13_j$ of the photoelectric conversion surface in the case where the measurement-object light is incident to the photodetector 110, based on pulse height distributions ($N_j(h)$) generated by the collector 300 upon setting in a normal measurement mode and with incidence of the measurement-object light to the photodetector, the pulse height distributions of single photoelectron events ($p_{1,j}(h)$) already obtained, and the pulse height distributions of k-photoelectron events ($p_{k,j}(h)$) already obtained, and thereby obtaining the intensity of the measurement-object light, (iv) a switch device 79 for receiving the pulse height distributions $N_j(h)$ output from the collector 300 and for outputting it in an alternative way to the generator 71 or to the estimating unit 73 in accordance with a data direction instruction signal SK, and (v) a measurement control unit 74 for giving an instruction of activation of the generator 71 in a collection mode of single photoelectron events and giving an instruction of activation of the estimating unit 73 in the normal measurement mode, and for outputting the operation timing signals (GT, SH, SL, AS, HS, HR) to the collector 300.

The apparatus of the present embodiment measures the intensity of the measurement-object light in the following manner.

Prior to measurement of the measurement-object light, the pulse height distributions $p_{i,j}(h)(1 \leq i \leq k_{MAX})$ for calibration are generated. For generation of the pulse height distributions $p_{i,j}(h)$, the calibration sample 920 is used.

The measurement control unit 74 first turns the memory reset signal HR temporarily significant, so as to reset the all contents of the histogramming memory 60 to the count value "0."

Figure 4:
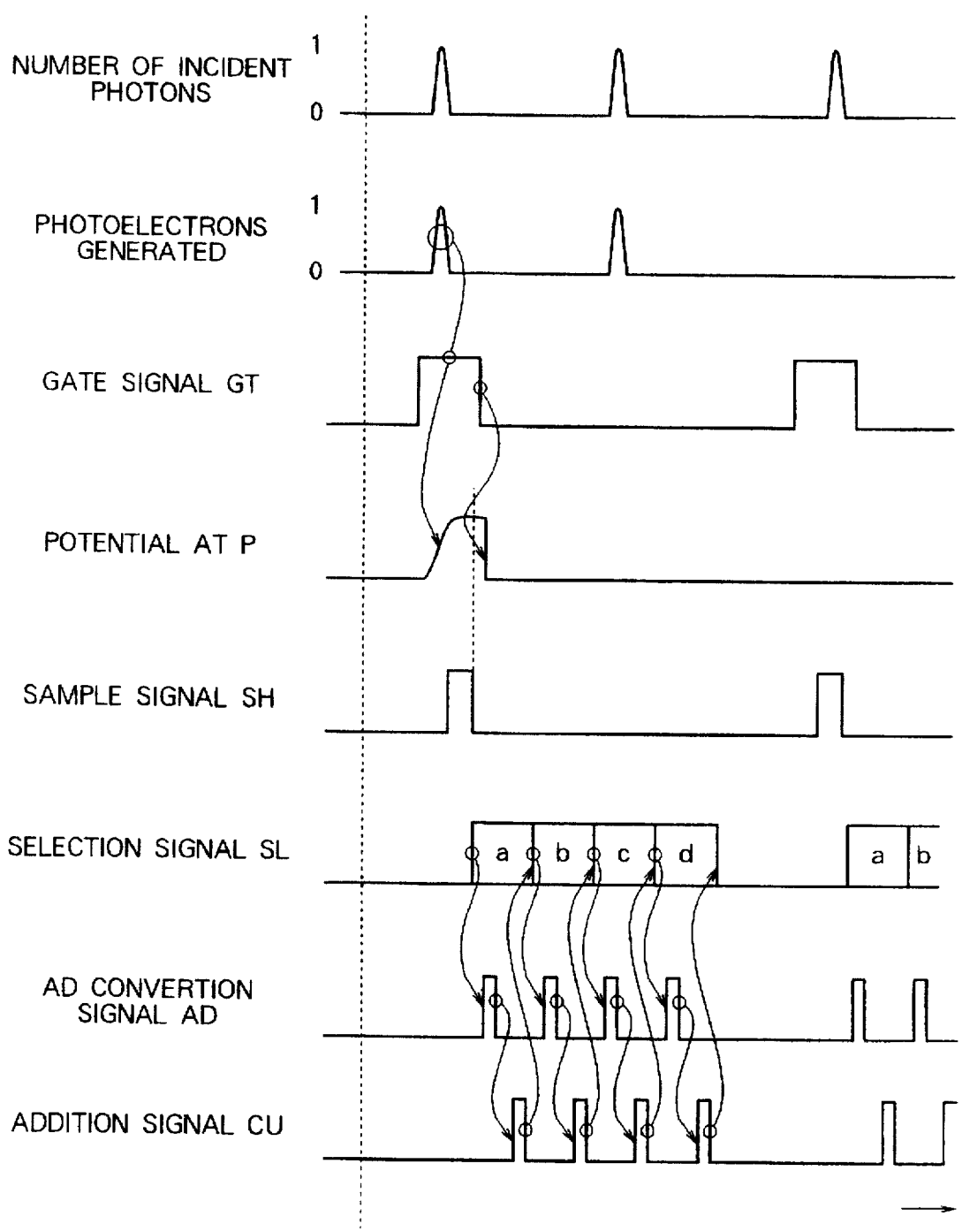
FIG. 4 is a timing chart to illustrate the operation upon collection of single photoelectron events in the light measuring apparatus of Embodiment 1.

The light emitted from the calibration sample 920 is incident through the spectroscope 410 and optical system 420 in order, to the photodetector 110. FIG. 4 is a timing chart to illustrate the operation of from incidence of light to the photodetector 110 up to generation of the pulse height distributions $N_{1,j}(h)$ in the collector 300.

In collection of one event, the measurement control unit 74 makes the gate signal GT, which is an integration instruction signal, significant throughout time $T_G$. During the significant period of the gate signal GT, switches 21 of integrators 20 are kept in an open state, whereby the current signals $I_j$ output from the photodetector 110 are integrated respectively and charges depending upon the current signals are accumulated in capacitors 22. Then potentials are built up at point P in accordance with the charges accumulated, and voltage signals are output.

The calibration sample 920 is adjusted so that it emits only light of very small quantity and, in most cases, only at most one photon is incident to each zone $13_j$ of the photoelectric conversion surface 13 in the photodetector 110 while the gate signal GT is kept significant. Accordingly, the number of photoelectrons generated in each zone $13_j$ of the photoelectric conversion surface during the significant period of gate signal GT is at most 1 in the most cases.

The voltage signal output from each integrator 20 is supplied to the amplifier 30 to be amplified and the amplified signal is supplied to the sample holder 40.

The measurement control unit 74 makes the sample instruction signal SH significant during the significant period of gate signal GT and changes the sample instruction signal SH from significant to non-significant immediately before the gate signal GT transitions from significant to non-significant.

Each sample holder 40 performs sampling in the significant state of the sample instruction signal SH and keeps holding in the non-significant state of the sample instruction signal SH the voltage value sampled at the time when the sample instruction signal SH is changed from significant to non-significant. Namely, the sample holder 40 keeps outputting the voltage value $V_j$ according to the potential value at point P immediately before transition of gate signal GT from significant to non-significant, after the sample instruction signal SH is changed from significant to non-significant. Then the voltage signals $V_j$ output from the sample holders 40 are supplied to the selector circuit 45.

After changing the sample instruction signal SH from significant to non-significant, the measurement control unit 74 first selects the voltage signal $V_a$ and histogramming memory unit $62_a$ by the selection signal SL. As a result, the voltage signal $V_a$ is input through the selector circuit 45 to the AD converter 50.

Subsequently, the measurement control unit 74 turns the AD conversion signal AD temporarily significant, thereby notifying the AD converter 50 of an execution instruction of AD conversion operation. The AD converter 50, instructed to execute the AD conversion operation, converts the input voltage value $V_a$, which is an analog value, to a digital value and outputs the digital signal carrying a pulse height value concerning the zone $13_a$ of the photoelectric conversion surface in one event.

The digital signal output from the AD converter 50 is supplied to the multi-channel histogramming memory 60. Since in the multi-channel histogramming memory 60 the data line to the histogramming memory unit $62_a$ is already set by the selection signal SL, the digital signal output from the AD converter 50 is input to the histogramming memory unit $62_a$.

Next, at a proper time after completion of the AD conversion operation of the AD converter 50, the measurement control unit 74 makes the addition signal CU temporarily significant to notify the histogramming memory unit $62_a$ of an addition instruction. The histogramming memory unit $62_a$, receiving the addition instruction, adds only 1 to the contents at an address according to the pulse height value input.

Then the voltage signal $V_b$ and histogramming memory unit $62_b$ are selected by the selection signal SL. As a result, the voltage signal $V_b$ is input through the selector circuit 45 into the AD converter 50. After that, similarly as in the case of the voltage signal $V_a$, only 1 is added to the contents at an address according to the pulse height value of the input pulse to the histogramming memory unit $62_b$.

Subsequently, successively selecting by the selection signal SL the voltage signal $V_c$ and histogramming memory unit $62_c$ and the voltage signal $V_d$ and histogramming memory unit $62_d$, similarly as in the case of the voltage signal $V_a$, only 1 is added to the contents at addresses according to pulse height values of input pulses to the histogramming memory unit $62_c$ and histogramming memory unit $62_d$.

After completion of the above operation of from change of gate signal GT to significant, to updating of the contents of the histogramming memory unit $62_a$-$62_d$, the operation of from again changing the gate signal GT to significant, to updating the contents of the histogramming memory unit $62_a$-$62_d$ is repeated a predetermined number of times, thereby generating the pulse height distributions $N_{1,j}(h)$ ($0 \leq h \leq h_{MAX}$) inside the histogramming memory units $62_j$.

After the pulse height distributions $N_{1,j}(h)$ are generated as described above, the pulse height distributions $p_{1,j}(h)$ ($1 \leq h \leq h_{MAX}$) of single photoelectron events are generated.

For generating the pulse height distributions $p_{1,j}(h)$, the measurement control unit 74 controls the switch device 79 by the data direction instruction signal SK to keep it in the state of 79A, thereby setting the destination of data of the pulse height distributions $N_{1,j}(h)$ output from the collector 300, to the generator 71. After that, the measurement control unit 74 turns the activation instruction signal SA significant to activate the generator 71.

Figure 5:
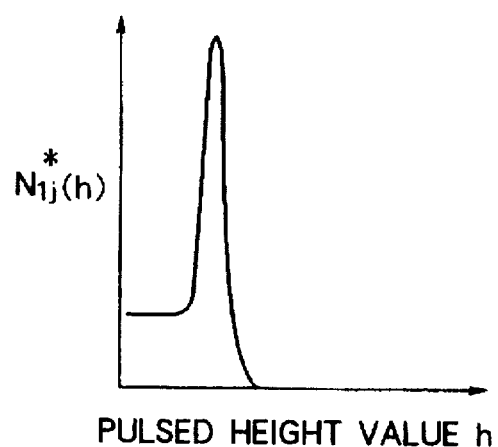
FIG. 5 is a graph to show the pulse height distribution $N^*_1(h)$.
Figure 6:
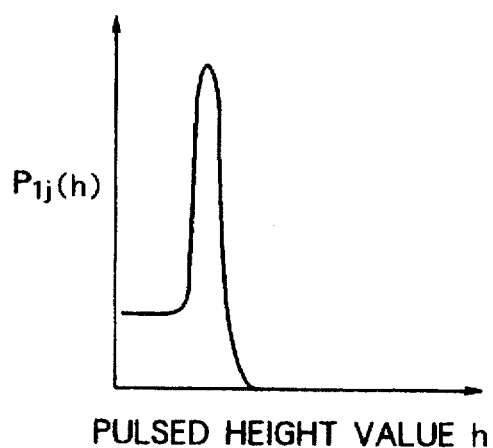
FIG. 6 is a graph to show the pulse height distribution $p_1(h)$.

The generator 71, thus activated, collects the data of pulse height distributions $N_{1,j}(h)$ from the collector 300, and in order to eliminate noise components or zero photoelectron events in the low pulse height portion, the generator 71 obtains $N^*_{1,j}(h)$ shown in FIG. 5, by extrapolation from values of the other pulse height portion. Then the generator 71 performs the following calculation to generate the pulse height distributions $p_{1,j}(h)$ of single photoelectron events shown in FIG. 6.

$$p_{1,j}(h) = N^*_{1,j}(h) / \left( \sum_{h=0}^{h_{MAX}} N^*_{1,j}(h) \right) \quad (3)$$

where $h_{MAX}$: the maximum of output digital value from the AD converter 50.

After the pulse height distributions $p_{1,j}(h)$ of single photoelectron events are generated as described above, the pulse height distributions $p_{k,j}(h)$ ($2 \leq k \leq k_{MAX}$) of k-photoelectron events are generated.

For generating the pulse height distributions $p_{k,j}(h)$, the measurement control unit 74 changes the activation instruction signal KA to significant, thereby activating the generator 72.

The generator 72, thus activated, collects the data of pulse height distributions $p_{1,j}(h)$ from the generator 71 and recursively calculates the following to generate the pulse height distributions $p_{k,j}(h)$ of k-photoelectron events.

$$p_{k,j}(h) = \sum_{l=0}^{h} (p_{k-1,j}(l) \cdot p_{1,j}(h-l)) \quad (2)$$

In the case of an arbitrary distribution being assumed upon estimation of photoelectron number distribution, letting $h_{peak\ 1,j}$ be the pulse height value giving the peak value of $p_{1,j}(h)$, $k_{MAX}$ is determined by $k_{MAX} = h_{MAX}/h_{peak\ 1,j}$. If $h_{MAX} = 4095$ and $h_{peak\ 1,j} = 400$, $k_{MAX}$ is approximately 10. If the photoelectron number distribution is assumed to be a Poisson distribution, $k_{MAX}$ is approximately 2 to 3 times $h_{MAX}/h_{peak\ 1,j}$. For example, if $h_{MAX} = 4095$ and $h_{peak\ 1,j} = 400$, $k_{MAX}$ is approximately 30 in this case. The ground that the pulse height distributions $p_{k,j}(h)$ can be obtained from the convolution calculation between the pulse height distributions $p_{k-1,j}(h)$ and $p_{1,j}(h)$ as described above is based on the fact that the pulse height distribution $p_{k,j}(h)$ indicates a distribution of numbers of electron-hole pairs obtained when k photoelectrons emitted in the photoelectric conversion surface $13_j$ enter the APD $15_j$ to be avalanche-multiplied.

If the spread of pulse height distribution caused by the noise generated in the photodetector 110, integrator 20, amplifier 30, sample hold circuit 40, and AD converter 50 cannot be ignored, the pulse height distributions $p_{k,j}(h)$ each are calculated by Eq. (3), based on the result of eliminating the influence of the noise from the pulse height distributions $p_{1,j}(h)$ by deconvolution calculation, and thereafter the influence of the noise is superimposed on each of the pulse height distributions $p_{k,j}(h)$ (k=2, 3, . . . , $k_{MAX}$) by convolution calculation.

Figure 7:
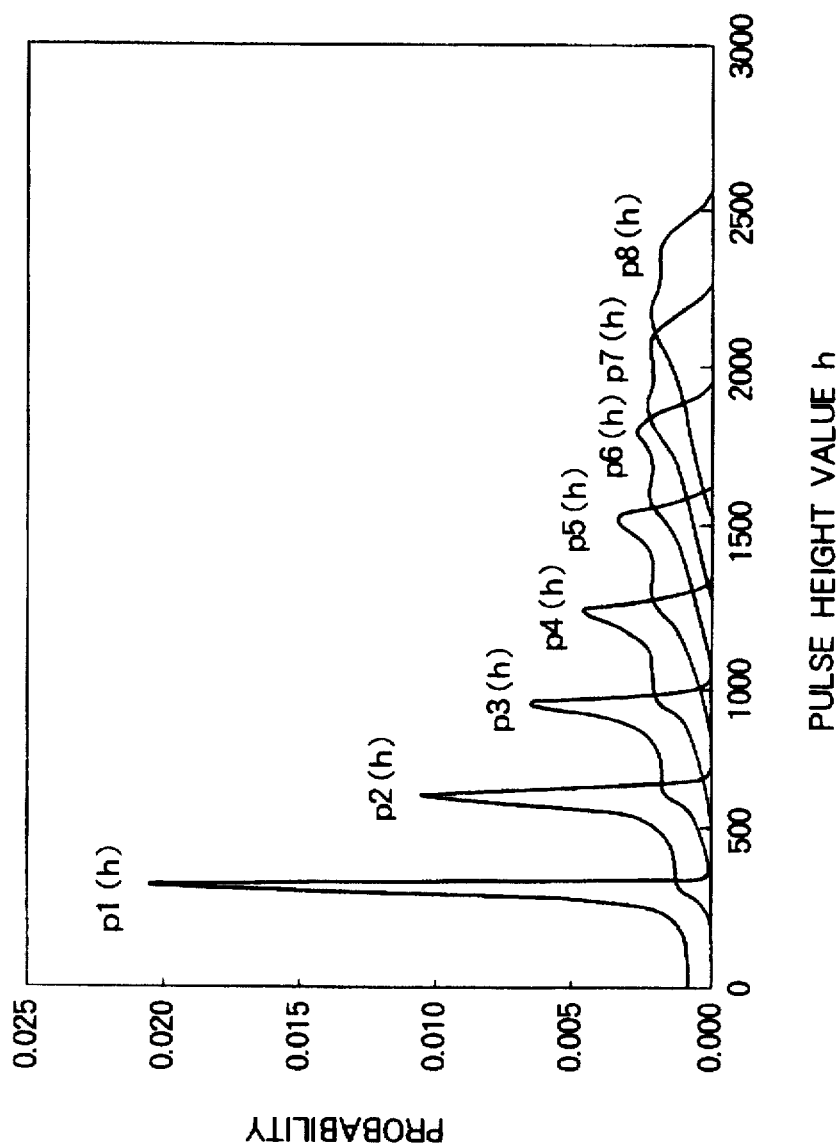
FIG. 7 is a graph to show the pulse height distributions $p_k(h)$ of k-photoelectron events.

As described above, the pulse height distributions $p_{i,j}(h)$ (i=1, 2, 3, . . . , $k_{MAX}$), with consideration on the influence of the noise which the light measuring apparatus inherently has, are prepared prior to estimation of photoelectron number distribution. FIG. 7 is a drawing to show the pulse height distributions $p_{k,j}(h)$ of k-photoelectron events obtained in this way.

After the pulse height distributions $p_{i,j}(h)$ (i=1, . . . , $k_{MAX}$) are generated as described above, the calibration sample 920 is replaced by the measurement object 910 and the measurement-object light from the measurement object 910 is measured.

The measurement control unit 74 first turns the memory reset signal HR temporarily significant to reset the all contents of histogramming memory 60 to the count value "0."

The light emitted from the measurement object 910 is incident through the spectroscope 410 and optical system 420 in order, to the photodetector 110.

For measuring the measurement-object light of high intensity and effectively utilizing this light measuring apparatus, the measurement-object light is not incident in a spot shape, but preferably incident over a wide area to the entrance window 12. Therefore, in the case of the beam diameter of the measurement-object light being small, the optical system 420 is preferably arranged to have a lens for magnifying the diameter of the measurement-object light in front of the entrance window. This arrangement can enlarge the measurement range of light quantity of measurement-object light while maintaining the excellent quantifying property.

However, in the case of measurement of measurement-object light of small quantity, if the measurement-object light is received by the entire area of the photoelectric conversion surface 13 to make photoelectrons incident to the APDs 15a–15d, a less number of photoelectrons will be incident to each APD, which requires more time and drops efficiency. In this case, measurement can be conducted within a short time and with good efficiency by employing such arrangement that the measurement-object light is made incident to only a certain limited zone in the photoelectric conversion surface 13 whereby photoelectrons are incident to one of the APDs 15a–15d and processing is carried out only for the current signal output from the APD to which the photoelectrons are made incident.

Figure 8:
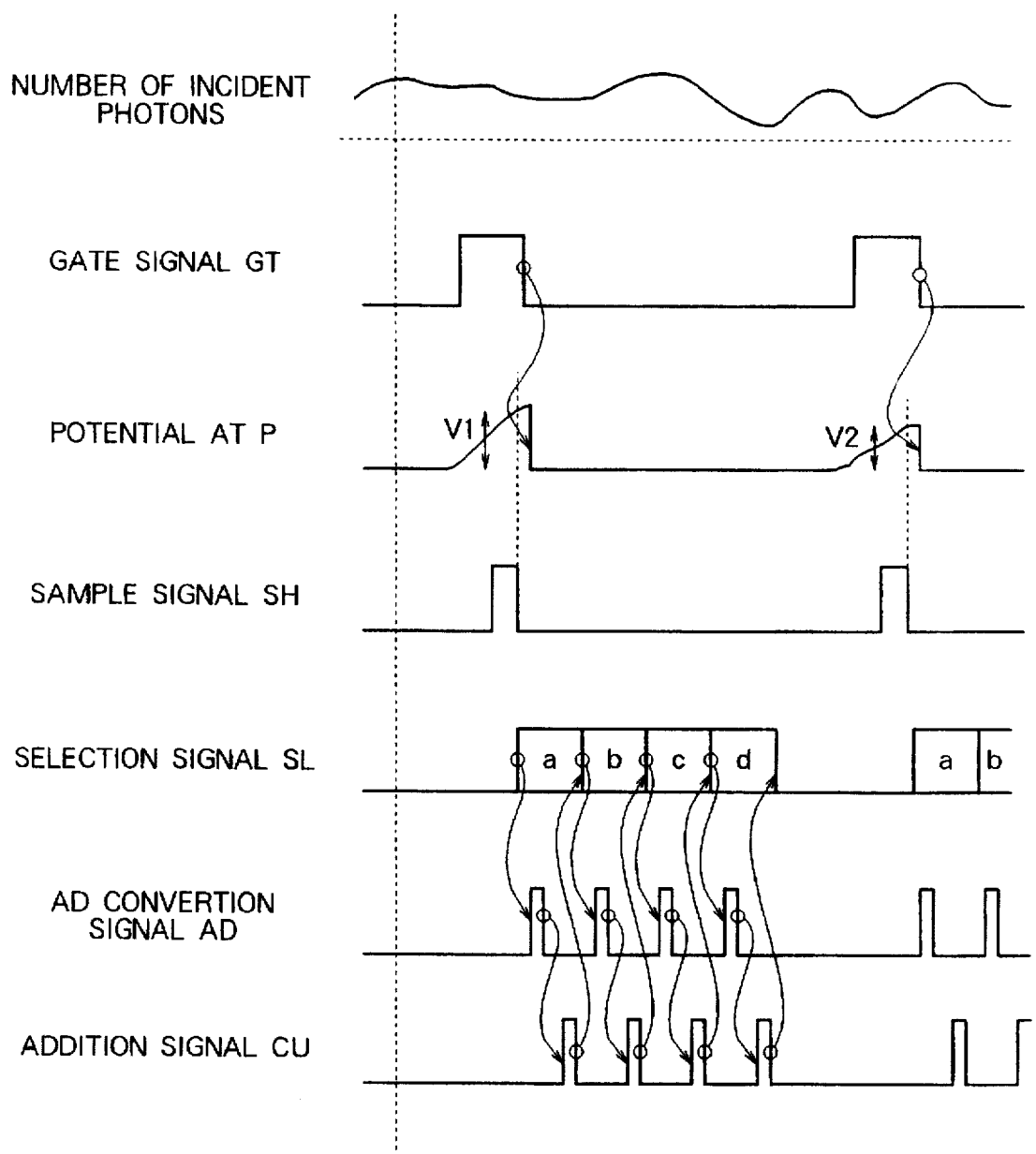
FIG. 8 is a timing chart to illustrate the operation upon measurement of measurement-object light in the light measuring apparatus of Embodiment 1.

FIG. 8 is a timing chart to illustrate the operation of from incidence of light to the photodetector 110 to generation of pulse height distributions N(h) output from the collector 300.

Similarly as in the case of measurement of single photoelectron events, the measurement control unit 74 sends the operation timing signals (GT, SH, SL, AD, CU, HR) to the collector 300. Accordingly, the collector 300 operates in the same manner as in the case of single photoelectron events, thereby generating the pulse height distributions $N_j(h)$ according to incidence of the measurement-object light inside the histogramming memory units $62_j$.

After the pulse height distributions $N_j(h)$ are generated as described above, estimated is a photoelectron number distribution generated in the photoelectric surface 13 in each event with incidence of the measurement-object light, thereby obtaining the intensity of the incident light.

For estimating the photoelectron number distribution, the measurement control unit 74 controls the switch device 79 by the data direction instruction signal SK to turn it to the state of 79B, whereby the destination of data of pulse height distributions $N_j(h)$ from the collector 300 is set to the estimating unit 73. After that, the measurement control unit 74 makes the activation instruction signal GA significant to activate the estimating unit 73.

The estimating unit 73, thus activated, collects the data of pulse height distributions $N_j(h)$ from the collector 300 and receives the pulse height distributions $p_{i,j}(h)$ from the generator 72, and the estimating unit 73 performs the following arithmetic using the pulse height distributions $N_j(h)$ and the pulse height distributions $p_{i,j}(h)$.

The pulse height distributions $N_j(h)$ do not have to be normalized and thus, they may be the same values as those accumulated in the histogramming memory units $62_j$. Namely, the pulse height distributions $N_j(h)$ indicate distributions of events having obtained the pulse height values h. For example, the maximum likelihood method is used for estimating the distribution of numbers of photoelectrons incident to each APD $15_j$, emitted in the photoelectric conversion surface 13 of photodetector 110 with incidence of the incident light (or for estimating the photoelectron number distribution). Namely, letting $q_{k,j}$(k=1, 2, 3, . . . , $k_{MAX}$) be a probability of occurrence of each of k-photoelectron events, $q_{k,j}$ is obtained which makes maximum the logarithmic likelihood expressed by Eq. (4) defined below, and it is used as an estimated photoelectron number distribution.

$$\log L = \left( N - \sum_{h=h_{min}}^{h_{MAX}} N_j(h) \right) \cdot \log(P_{ND_j}) + \sum_{h=h_{min}}^{h_{MAX}} N_j(h) \cdot \log\{p_j(h)\} \quad (4)$$

Here, N is the number of measurements (i.e., the number of significant turns of gate signal GT), and $h_{min}$ is a minimum pulse height value h that can be used for analysis. If the pulse height value h is small, it cannot be used for analysis because of superposition of the noise caused by the APD $15_j$, amplifier 30, etc. Thus, analysis is carried out only with values exceeding the pulse height value $h_{min}$. Further, $p_j(h)$ and $p_{ND_j}$ are given as follows.

$$p_j(h) = \sum_{k=1}^{K} q_{k,j} \cdot p_{k,j}(h) \quad (5)$$

$$p_{ND_j} = 1 - \sum_{h=h_{min}}^{h_{MAX}} p_j(h) \quad (6)$$

This $p_j(h)$ indicates an occurrence probability distribution of pulse height value h also taking account of occurrence probabilities (photoelectron number distribution) of respective k-photoelectron events (k=1, 2, 3, . . . , K). For obtaining $q_{k,j}$ to maximize the logarithmic likelihood of Eq. (4), a numerical computation method, for example the quasi Newton method, used for optimization problem is applied.

If the photoelectron number distribution is assumed to be a Poisson distribution, probabilities $q_{k,j}$ of occurrence of respective k-photoelectron events are expressed as follows.

$$q_{k,j} = \frac{\lambda_j^k}{k!} \exp(-\lambda_j) \quad (7)$$

Figure 9:
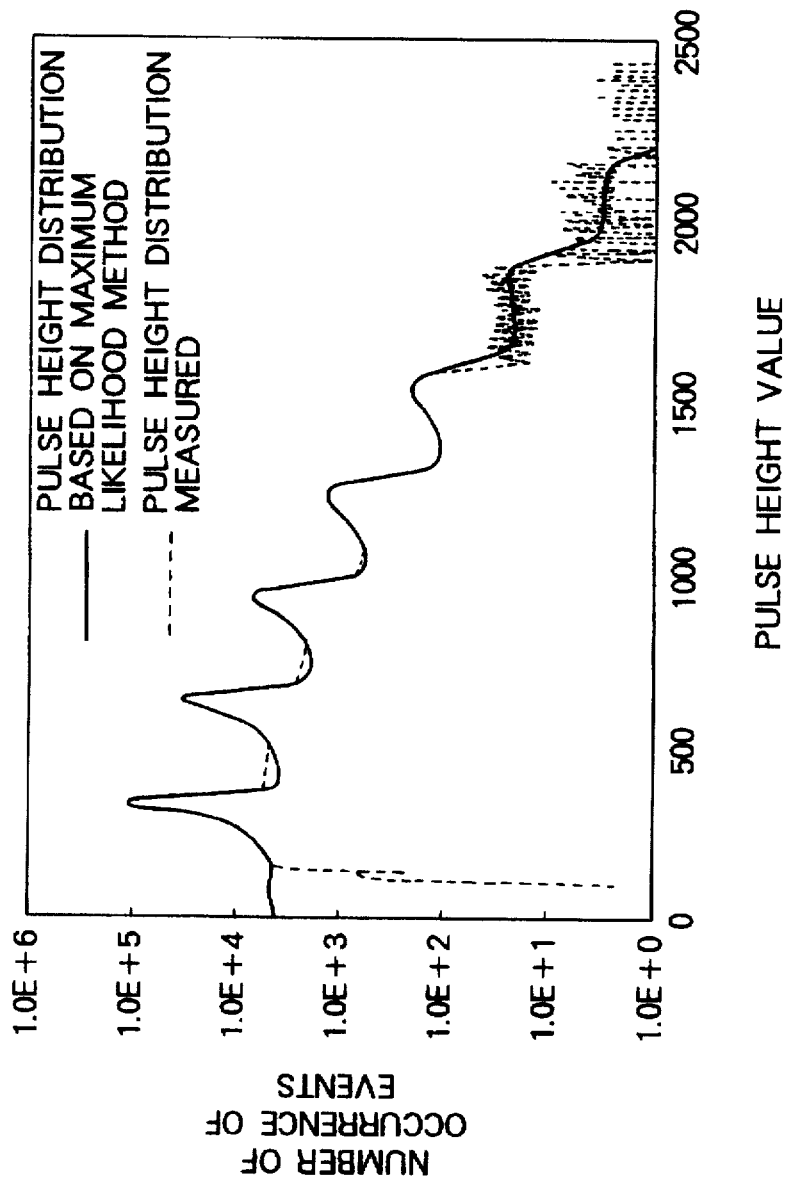
FIG. 9 is a drawing to show a pulse height distribution obtained by measuring the measurement-object light (dashed line) and a pulse height distribution calculated based on the $\lambda$ value estimated by the maximum likelihood method (solid line)

Here, $\lambda_j$ is a mean value of numbers of photoelectrons incident to APD $15_j$. In this case, obtaining the photoelectron number distribution to maximize the logarithmic likelihood is equivalent to obtaining the $\lambda_j$ value to maximize the logarithmic likelihood, which can be obtained by numerical computation, for example, such as the golden section method or the like. In the following description the photoelectron number distribution is assumed to be a Poisson distribution. FIG. 9 shows an example of the pulse height distribution (dashed line) generated in the histogramming memory units $62_j$ with reception of the measurement-object light by the photodetector 110 and the pulse height distribution based on the calculated based on the $\lambda_j$ value estimated by the maximum likelihood method. They show good agreement in the range of not less than the pulse height value $h_{min}$ (=150). The mean value λ of photoelectron numbers estimated at this time was 1.03.

Obtained as described above is the distribution of numbers of photoelectrons incident to the APD $15_j$ (the photoelectron number distribution), i.e., the mean value of numbers of photoelectrons incident thereto. The mean value of numbers of photoelectrons incident to each APD 15a–15d is a mean value of numbers of photoelectrons emitted in each zone $13_a$–$13_d$ of the photoelectric conversion surface 13 opposed to each APD 15a–15d, which indicates the intensity of the measurement-object light incident to that zone. Therefore, from the mean values of numbers of photoelectrons incident to the respective APDs 15a–15d, an intensity distribution of the measurement-object light having entered the photoelectric conversion surface 13 can be obtained, and the sum of intensities of the measurement-object light having entered the photoelectric conversion surface 13 can be obtained from the sum of numbers of photoelectrons having entered the respective APDs 15a–15d.

With measuring the intensity of the measurement-object light in this way, even if a large number of photoelectrons are emitted with incidence of the measurement-object light to the photoelectric conversion surface of photodetector, electron-hole pairs are avalanche-multiplied in each of plural APDs, whereby the intensity of the measurement-object light can be measured with accuracy.

If a spectrum is measured as scanning selected output wavelengths of spectroscope 410 as described above, provision of the plural APDs expands the incident light intensity range that can be detected with accuracy by the photodetector. Therefore, even if a difference is great between peak intensities of the spectrum of the measurement-object light, the spectrum can be measured with accuracy.

(Embodiment 2)

Figure 10:
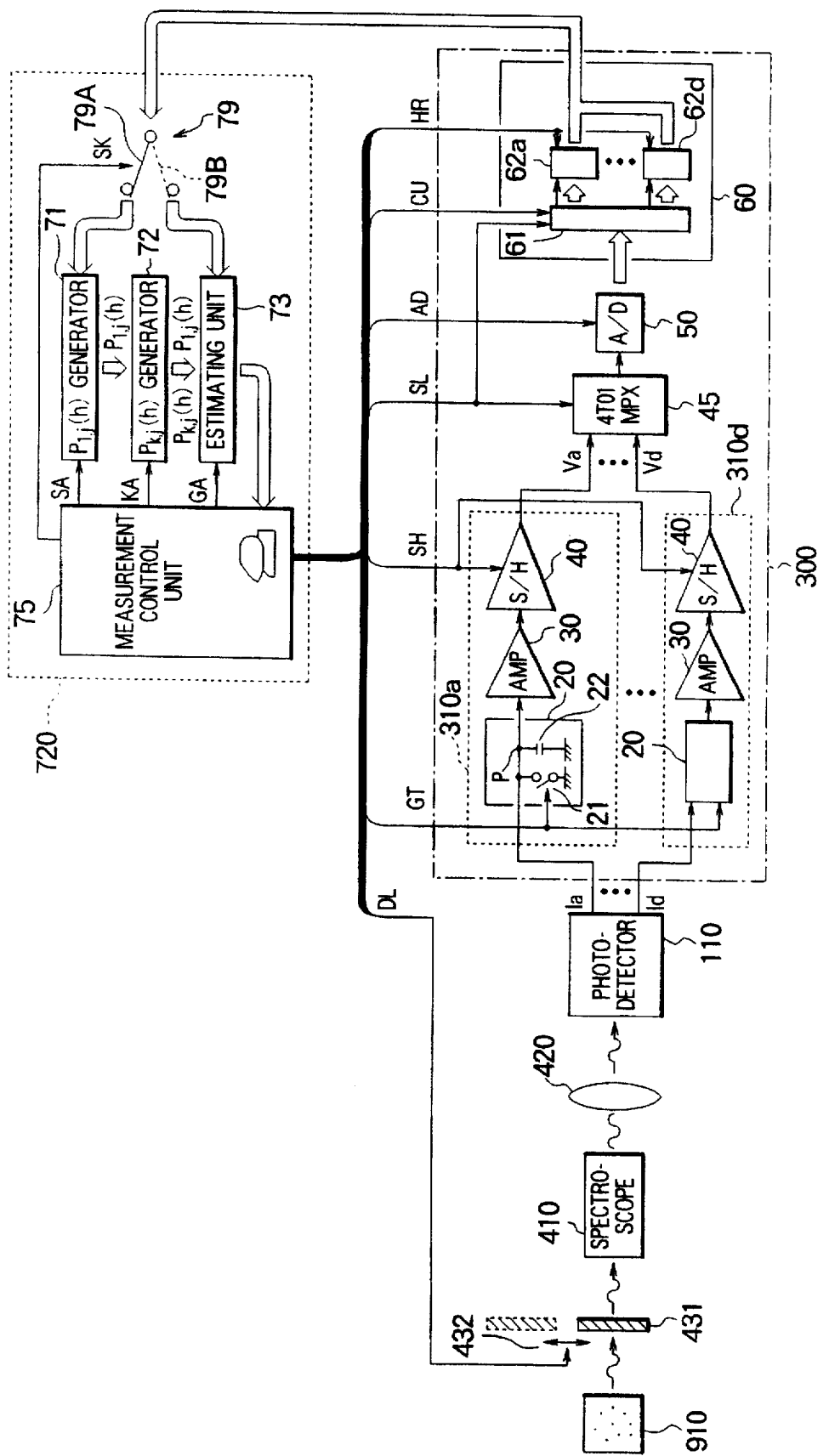
FIG. 10 is a structural drawing of a light measuring apparatus according to Embodiment 2 of the present invention.

FIG. 10 is a structural drawing of Embodiment 2 of the light measuring apparatus according to the present invention. The apparatus of the present embodiment is different from Embodiment 1 in that measurement of the measurement-object light is carried out without a need for the calibration sample. Because of this difference of function, the apparatus of the present embodiment is different from that of Embodiment 1 of FIG. 1 in that the apparatus of the present embodiment further comprises (i) a light reducing filter 431, and (ii) a carrier 432 for carrying the light reducing filter 431 in accordance with a light reducing instruction signal DL and the processing section 720 comprises a measurement control unit 75 for sending the light reducing instruction signal DL to the carrier 432, as shown in FIG. 10.

The apparatus of the present embodiment measures the intensity of the measurement-object light in the following manner.

Similarly as in Embodiment 1, prior to the measurement of the measurement-object light, the pulse height distributions for calibration $p_{i,j}(h)(1 \leq i \leq k_{MAX})$ are generated. For generating the pulse height distributions $p_{i,j}(h)$, the measurement control unit 75 changes the light reducing instruction signal DL to significant to control the carrier 432 so as to locate the light reducing filter 431 on the optical path before the measurement-object light from the measurement object 910 is incident to the photodetector 110.

After that, the pulse height distributions $p_{i,j}(h)$ ($1 \leq i \leq k_{MAX}$) are generated by the same operation as in Embodiment 1.

After the pulse height distributions $p_{i,j}(h)(1 \leq i \leq k_{MAX})$ are generated in this way, the measurement control unit 75 turns the light reducing instruction signal DL non-significant to control the carrier 432 so as to remove the light reducing filter 431 from the optical path before the measurement-object light from the measurement object 910 is incident to the photodetector 110, thereby letting the measurement-object light directly enter the photodetector 110.

After that, the same operation as in Embodiment 1 is carried out to estimate the photoelectron number distribution of photoelectrons generated in each zone $13_a$–$13_d$ of photoelectric conversion surface 13 with incidence of the measurement-object light thereto, thereby obtaining the intensity of the measurement-object light.

(Embodiment 3)

Figure 11:
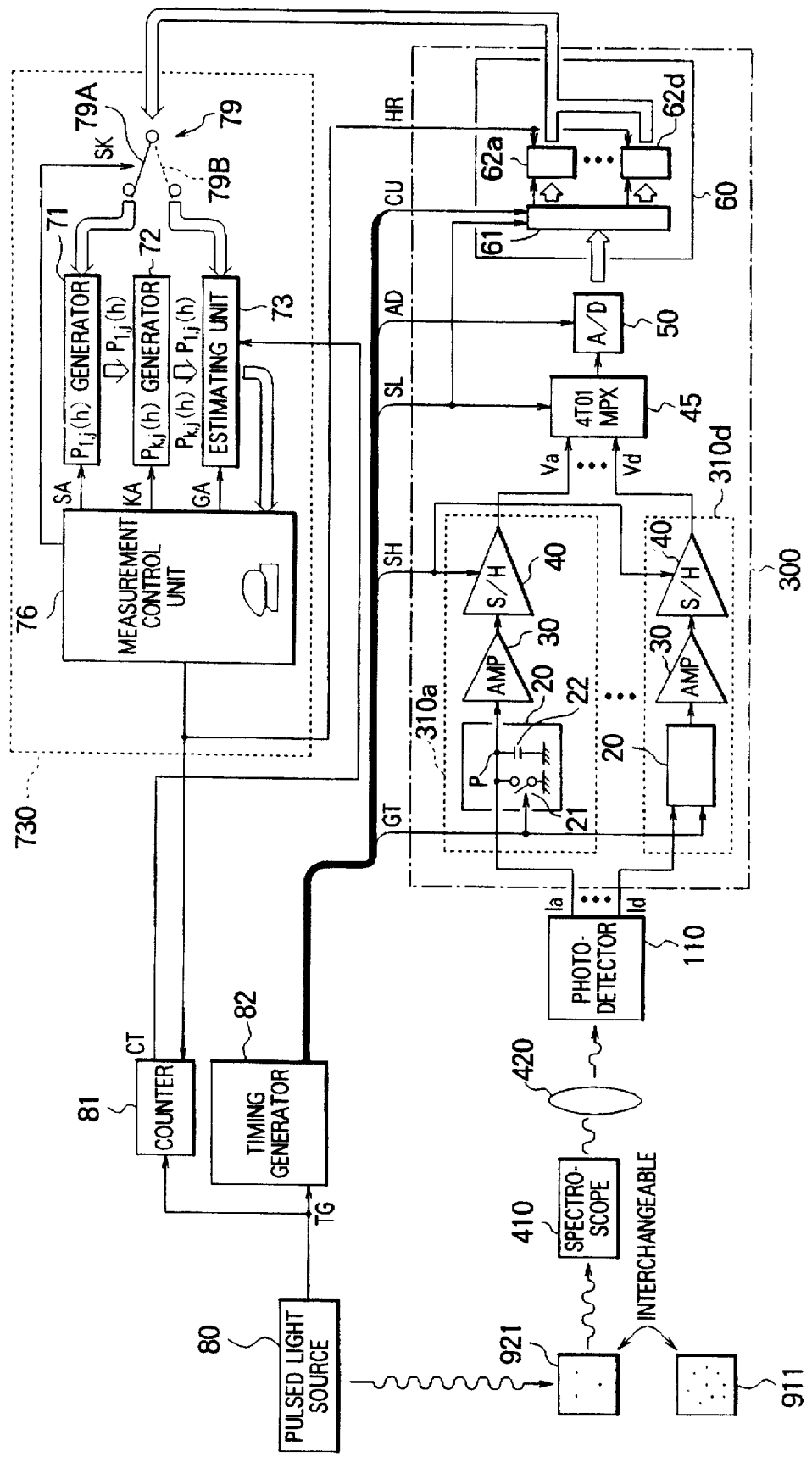
FIG. 11 is a structural drawing of a light measuring apparatus according to Embodiment 3 of the present invention.

FIG. 11 is a structural drawing of Embodiment 3 of the light measuring apparatus according to the present invention. The apparatus of the present embodiment is arranged to measure fluorescence emitted not spontaneously from the measured object but by irradiation with excitation light. Then the fluorescence is measured as measurement-object light.

As shown in FIG. 11, the apparatus of the present embodiment comprises (a) a spectroscope 410 for receiving fluorescence from a measured object 911 or from a calibration sample 921, generated upon irradiation with excitation light, separating it, and emitting light of wavelengths becoming a measurement object, (b) a photodetector 110 for receiving the measurement-object light emitted from the spectroscope 410 and coming through the optical system 420, emitting photoelectrons in the number according to a distribution of photoelectron numbers depending upon the number of photons of incident light, multiplying photoelectrons emitted from each of plural zones in the photoelectric conversion surface emitting the photoelectrons, and outputting pulse current signals $I_j$ (j=a to d) of every zone of the photoelectric conversion surface, (c) a collector 300 for collecting the pulse height values of pulse current signals $I_j$ of each event and generating pulse height distributions ($N_j(h)$; h is pulse height values) of event number against pulse height value, (d) a pulsed light source 80 for outputting excitation pulsed light and a generation timing signal TG of the pulsed light, (e) a counter 81 for receiving the generation timing signal TG and counting the number of generation times of the pulsed light of the pulsed light source 80, (f) a timing generating circuit 82 for receiving the generation timing signal TG and outputting the operation timing signals (GT, SH, SL, AD, CU) to the integrators 20 and to the collector 300, and (g) a processing section 730 for collecting the pulse height distributions ($N_j(h)$) generated by the collector 300 to process them and outputting a reset signal HR to the collector 300 and to the counter 81.

The processing section 730 comprises (i) a generator 71 activated in accordance with an activation instruction signal SA to generate pulse height distributions ($p_{1,j}(h)$) of single photoelectron events, based on the pulse height distributions ($N_{1,j}(h)$) generated by the collector 300, (ii) a generator 72 for generating pulse height distributions ($p_{k,j}(h)$) of k-photoelectron events, in each of which the number of photoelectrons emitted in the photodetector 110 is k ($2 \leq k \leq k_{MAX}$), based on the pulse height distributions ($p_{1,j}(h)$) of single photoelectron events, (iii) an estimating unit 73 for estimating a photoelectron number distribution of each zone $13_a$–$13_d$ of photoelectric conversion surface for a case in which the measurement-object light is incident to the photodetector 110, based on pulse height distributions ($N_j(h)$) generated by the collector 300 when the measurement-object light is incident to the photodetector in the case of setting in the normal measurement mode, the pulse height distributions ($p_{1,j}(h)$) of single photoelectron events already obtained, and the pulse height distributions ($p_{k,j}(h)$) of k-photoelectron events already obtained, thereby obtaining the intensity of the measurement-object light, (iv) a switch device 79 for receiving the pulse height distributions $N_j(h)$ output from the collector 300 and outputting them in an alternative way to the generator 71 or to the estimating unit 73 in accordance with the data direction instruction signal SK, and (v) a measurement control unit 76 for giving an instruction of activation of the generator 71 in the case of the collection mode of single photoelectron events and giving an instruction of activation of the estimating unit 73 in the case of the normal measurement mode, and for outputting the reset signal HR to the collector 300 and to the counter 81.

The apparatus of the present embodiment measures the intensity of the measurement-object light in the following manner.

Prior to the measurement of the measurement-object light, pulse height distributions for calibration, $p_{i,j}(h)$ ($1 \leq i \leq k_{MAX}$), are generated. For generating the pulse height distributions $p_{i,j}(h)$, the calibration sample 921 is used.

The measurement control unit 76 first makes the memory reset signal temporarily significant to reset the all contents of the histogramming memory units $62_j$, and the counter 81 to the count value "0." Then the pulsed light source 80 regularly outputs the excitation pulsed light, and the timing signal TG a little earlier than emission of the excitation pulsed light.

The timing generating circuit 82, receiving the timing signal TG, changes the gate signal GT to significant and then awaits arrival of incident light to the photodetector 110.

Figure 12:
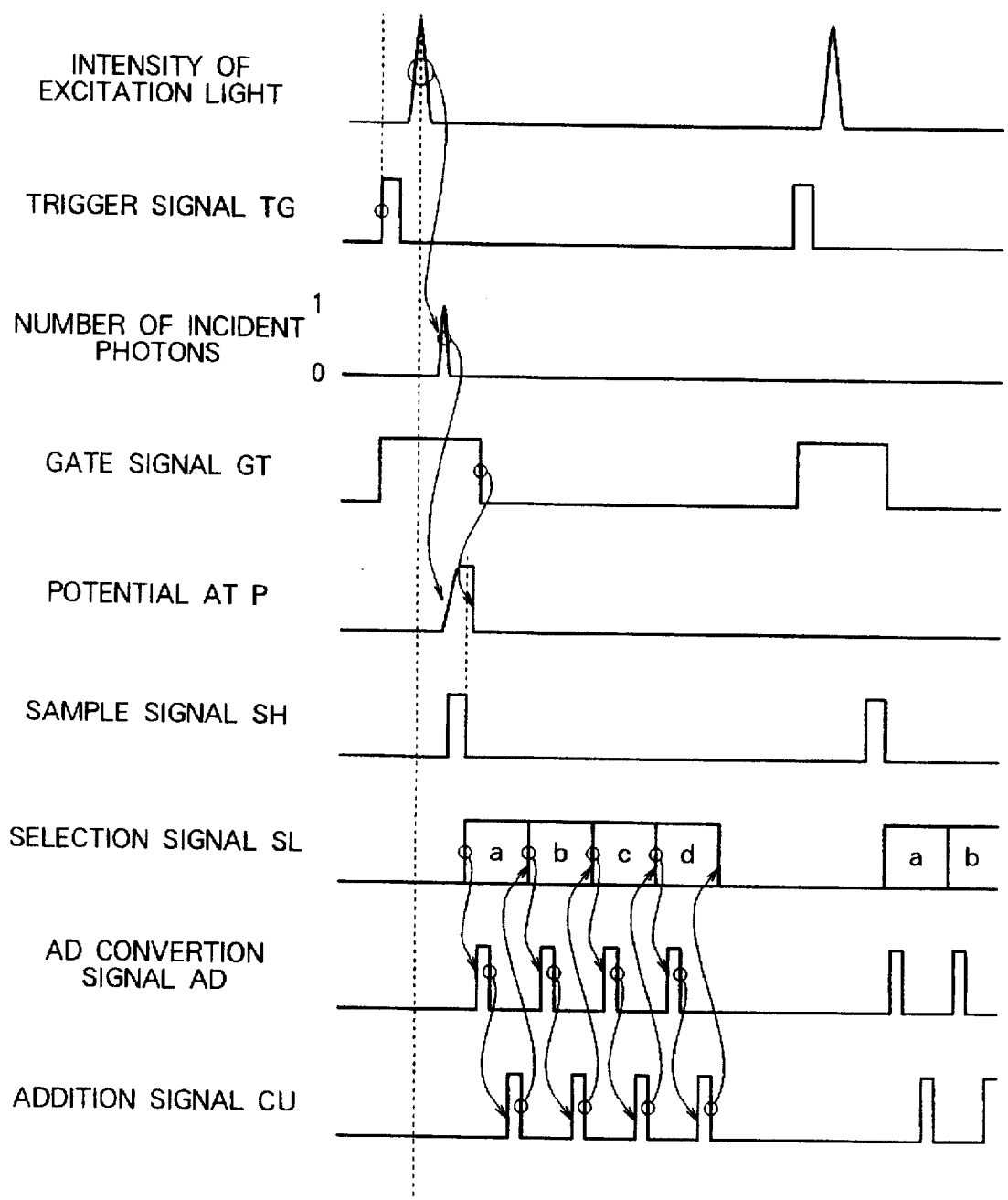
FIG. 12 is a timing chart to illustrate the operation upon collection of single photoelectron events in the light measuring apparatus of Embodiment 3.

The fluorescence, generated with irradiation of the calibration sample 921 after the excitation pulsed light is emitted from the pulsed light source 80, is incident through the spectroscope 410 and optical system 420 in order, to the photodetector 110. FIG. 12 is a timing chart to illustrate the operation of from incidence of light to the photodetector 110, to generation of the pulse height distributions $N_{1,j}(h)$ in the collector 300.

In collection of one event, the timing generating circuit 82 keeps the gate signal GT, which is an integration instruction signal, significant over the time $T_G$. During the significant period of the gate signal GT the switches 21 of integrators 20 are kept in an open state and the current signals $I_j$ output from the photodetector 110 are integrated respectively, so as to accumulate charges depending upon the current signals in the capacitors 22. Then potentials are raised at point P in accordance with the charges accumulated, and voltage signals are output.

The calibration sample 921 is adjusted so that it emits only light of very small quantity and, in most cases, only at most one photon is incident to each zone $13_j$ of the photoelectric conversion surface 13 in the photodetector 110 while the gate signal GT is kept significant. Accordingly, the number of photoelectrons generated in each zone $13_j$ of the photoelectric conversion surface $13_j$ during the significant period of gate signal GT is at most 1 in the most cases.

Each amplifier 30 receives the voltage signal output from the integrator 20 to amplify it and supplies the amplified signal to the sample holder 40.

The timing generating circuit 82 makes the sample instruction signal SH significant during the significant period of gate signal GT and changes the sample instruction signal SH from significant to non-significant immediately before the gate signal GT transitions from significant to non-significant.

The sample holder 40 performs sampling in the significant state of sample instruction signal SH and keeps holding in the non-significant state of sample instruction signal SH the voltage value sampled at the time when the sample instruction signal SH transitions from significant to non-significant. Namely, the sample holder 40 keeps outputting the voltage value $V_j$ according to the potential value at point P immediately before transition of gate signal GT from significant to non-significant, after the sample instruction signal SH is changed from significant to non-significant. Then the voltage signals $V_j$ output from the sample holders 40 are supplied to the selector circuit.

After changing the sample instruction signal SH from significant to non-significant, the timing generation circuit 82 first selects the voltage signal $V_a$ and histogramming memory unit $62_a$ by the selection signal SL. As a result, the voltage signal $V_a$ is input through the selector circuit 45 into the AD converter 50.

Subsequently, the timing generating circuit 82 turns the AD conversion signal AD temporarily significant to notify the AD converter 50 of an instruction of execution of the AD conversion operation. The AD converter 50, instructed to execute the AD conversion operation, converts the input voltage value $V_a$, which is an analog value, to a digital value, and outputs the digital signal carrying the pulse height value concerning the zone $13_a$ of the photoelectric conversion surface, in one event.

The digital signal output from the AD converter 50 is input into the multi-channel histogramming memory 60. Since in the multi-channel histogramming memory 60 the data line to the histogramming memory unit $62_a$ is set by the selection signal SL, the digital signal output from the AD converter 50 is input into the histogramming memory unit $62_a$.

Next, at a proper time after completion of the AD conversion operation of the AD converter 50, the timing generating circuit 82 turns the addition signal CU temporarily significant to notify the histogramming memory unit $62_a$ of an addition instruction. Receiving the addition instruction, the histogramming memory unit $62_a$ adds only 1 to the contents at an address according to the pulse height value input.

Then the voltage signal $V_b$ and histogramming memory unit $62_b$ are selected by the selection signal SL. As a result, the voltage signal $V_b$ is input through the selector circuit 45 into the AD converter 50. After that, similarly as in the case of the voltage signal $V_a$, only 1 is added to the contents at an address according to the pulse height value of the input pulse to the histogramming memory unit $62_b$.

Subsequently, successively selecting by the selection signal SL the voltage signal $V_c$ and histogramming memory unit $62_c$ and the voltage signal $V_d$ and histogramming memory unit $62_d$, similarly as in the case of the voltage signal $V_a$, only 1 is added to the contents at addresses according to pulse height values of input pulses to the histogramming memory unit $62_c$ and histogramming memory unit $62_d$.

After completion of the above operation of from changing the gate signal GT to significant, to updating the contents of the histogramming memory units $62_a$–$62_d$, the operation of from again changing the gate signal GT to significant, to updating the contents of histogramming memory units $62_a$–$62_d$ is repeated a predetermined number of times, thereby generating the pulse height distributions $N_{1,j}(h)$ ($0 \leq h \leq h_{MAX}$) inside the histogramming memory units $62_j$.

As described above, the pulse height distributions $p_{1,j}(h)$ ($1 \leq h \leq h_{MAX}$) of single photoelectron events are generated after generation of pulse height distributions $N_{1,j}(h)$.

After that, the pulse height distributions $p_{i,j}(h)$ are generated in the same manner as in Embodiment 1.

Subsequently, the calibration sample 921 is replaced by the measurement object 911 to measure the measurement-object light from the measurement object 911.

The measurement control unit 76 first makes the reset signal HR temporarily significant to reset the all contents of the histogramming memory 60 and counter 81 to the count value "0." Then the pulsed light source 80 regularly outputs the excitation pulsed light, and the timing signal TG a little earlier than emission of the excitation pulsed light.

The counter 81, receiving the timing signal TG, adds only 1 to the contents of the counter. The timing generating circuit 82, receiving the timing signal TG, turns the gate signal GT significant and awaits incidence of the measurement-object light to the photodetector 110.

Figure 13:
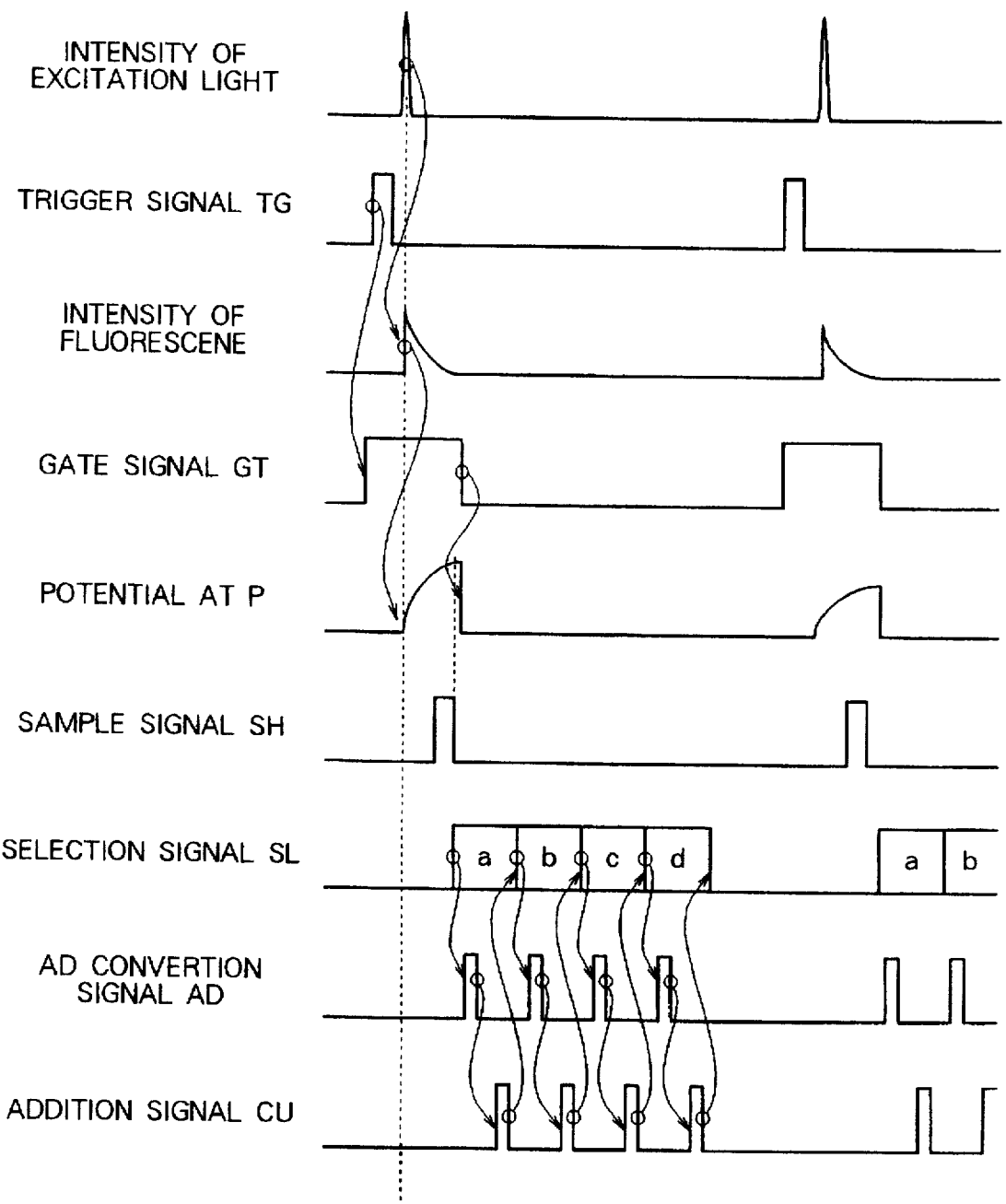
FIG. 13 is a timing chart to illustrate the operation upon measurement of measurement-object light in the light measuring apparatus of Embodiment 3.

The measurement-object light, generated with irradiation of the measurement object 911 after the excitation pulsed light is emitted from the pulsed light source 80, is incident through the spectroscope 410 and optical system 420 in order, to the photodetector 110. FIG. 13 is a timing chart to illustrate the operation of from incidence of light to the photodetector 110, to generation of the pulse height distributions $N_{1,j}(h)$ output from the collector 300.

The timing generating circuit 82 transfers the operation timing signals (GT, SH, SL, AD, CU, HR) to the collector 300 in the same manner as in the case of measurement of single photoelectron events. Accordingly, the collector 300 operates in the same manner as in the case of single photoelectron events to generate the pulse height distributions $N_j(h)$ according to incidence of the measurement-object light, inside the histogramming memory units $62_j$.

After the pulse height distributions $N_j(h)$ are generated as described above, the photoelectron number distribution of photoelectrons generated in each zone $13_j$ of the photoelectric conversion surface in each event is estimated in the same manner as in Embodiment 1, thus obtaining the intensity of incident light.

(Embodiment 4)

Figure 14:
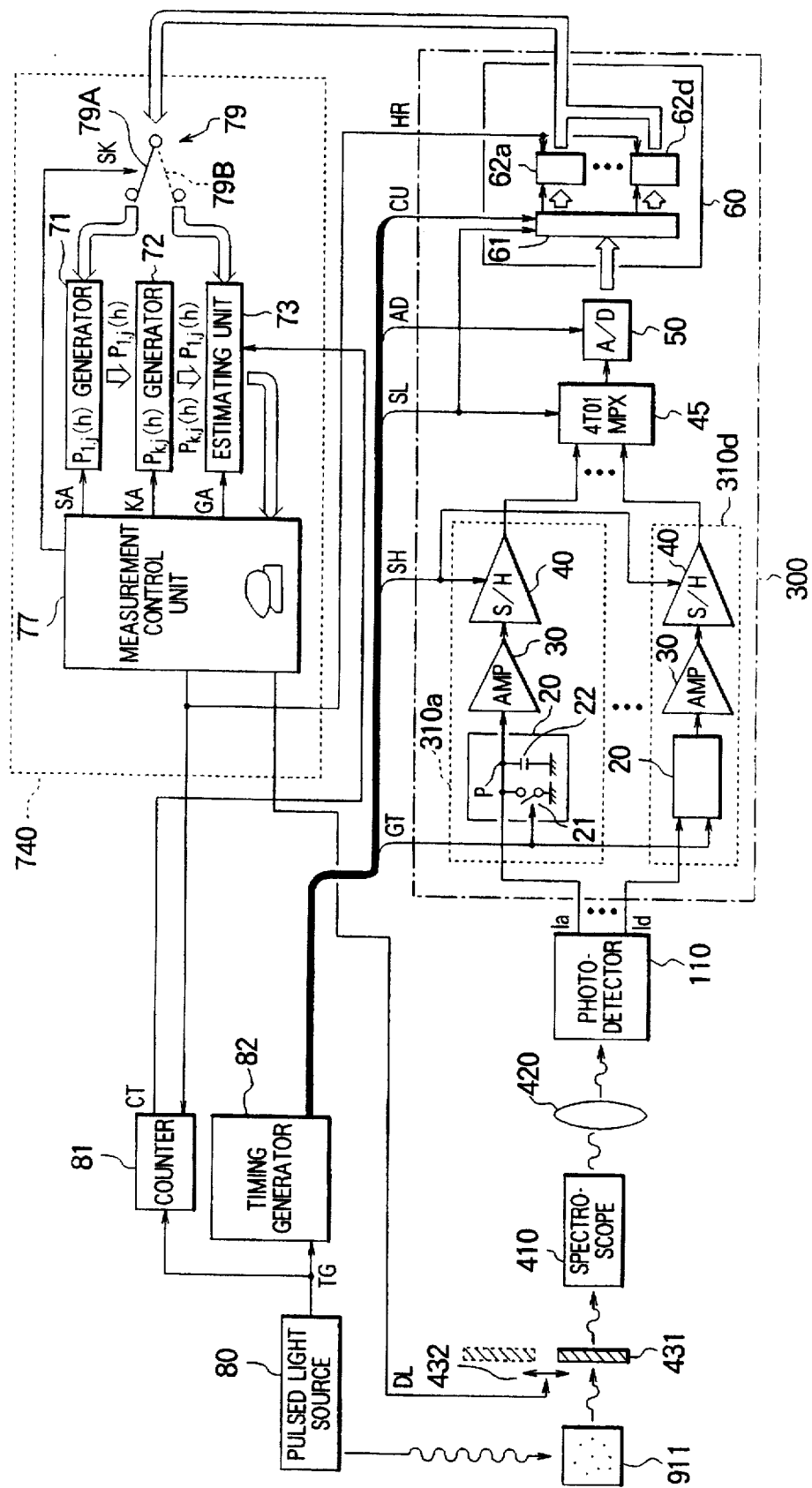
FIG. 14 is a structural drawing of a light measuring apparatus according to Embodiment 4 of the present invention.

FIG. 14 is a structural drawing of Embodiment 4 of the light measuring apparatus according to the present invention. The apparatus of the present embodiment is different from Embodiment 3 in that measurement of the measurement-object light is carried out without a need for the calibration sample. Because of this difference of function, the apparatus of the present embodiment is different from Embodiment 3 of FIG. 11 in that the apparatus further comprises (i) a light reducing filter 431 and (ii) a carrier 432 for moving the light reducing filter 431 in accordance with the light reducing instruction signal DL and in that the processing section 740 comprises a measurement control unit 77 for notifying the carrier 432 of the light reducing instruction signal DL, as shown in FIG. 14. In other words, the present embodiment is one attained by applying the modification of from Embodiment 1 to Embodiment 2, to Embodiment 3.

The apparatus of the present embodiment measures the intensity of the measurement-object light in the following manner.

Similarly as in Embodiment 3, the pulse height distributions for calibration, $p_{i,j}(h)(1 \leq i \leq k_{MAX})$, are generated prior to the measurement of the measurement-object light. For generating the pulse height distributions $p_{i,j}(h)$, the measurement control unit 77 makes the light reducing instruction signal DL significant to control the carrier 432, so as to locate the light reducing filter 431 on the optical path before the measurement-object light from the measurement object 911 is incident to the photodetector 110.

After that, the same operation as in Embodiment 3 is carried out to generate the pulse height distributions $p_{i,j}(h)$ $(1 \leq i \leq k_{MAX})$.

After the pulse height distributions $p_{i,j}(h)(1 \leq i \leq k_{MAX})$ are generated in this way, the measurement control unit 77 makes the light reducing instruction signal DL non-significant to control the carrier 432 so as to remove the light reducing filter 431 from the optical path before the measurement-object light from the measurement object 911 is incident to the photodetector 110, thereby letting the measurement-object light directly enter the photodetector 110.

After that, the same operation as in Embodiment 3 is carried out to estimate the photoelectron number distribution of photoelectrons occurring in each zone $13_j$ of the photoelectric conversion surface with incidence of the measurement-object light, thereby obtaining the intensity of the measurement-object light.

(Embodiment 5)

Figure 15:
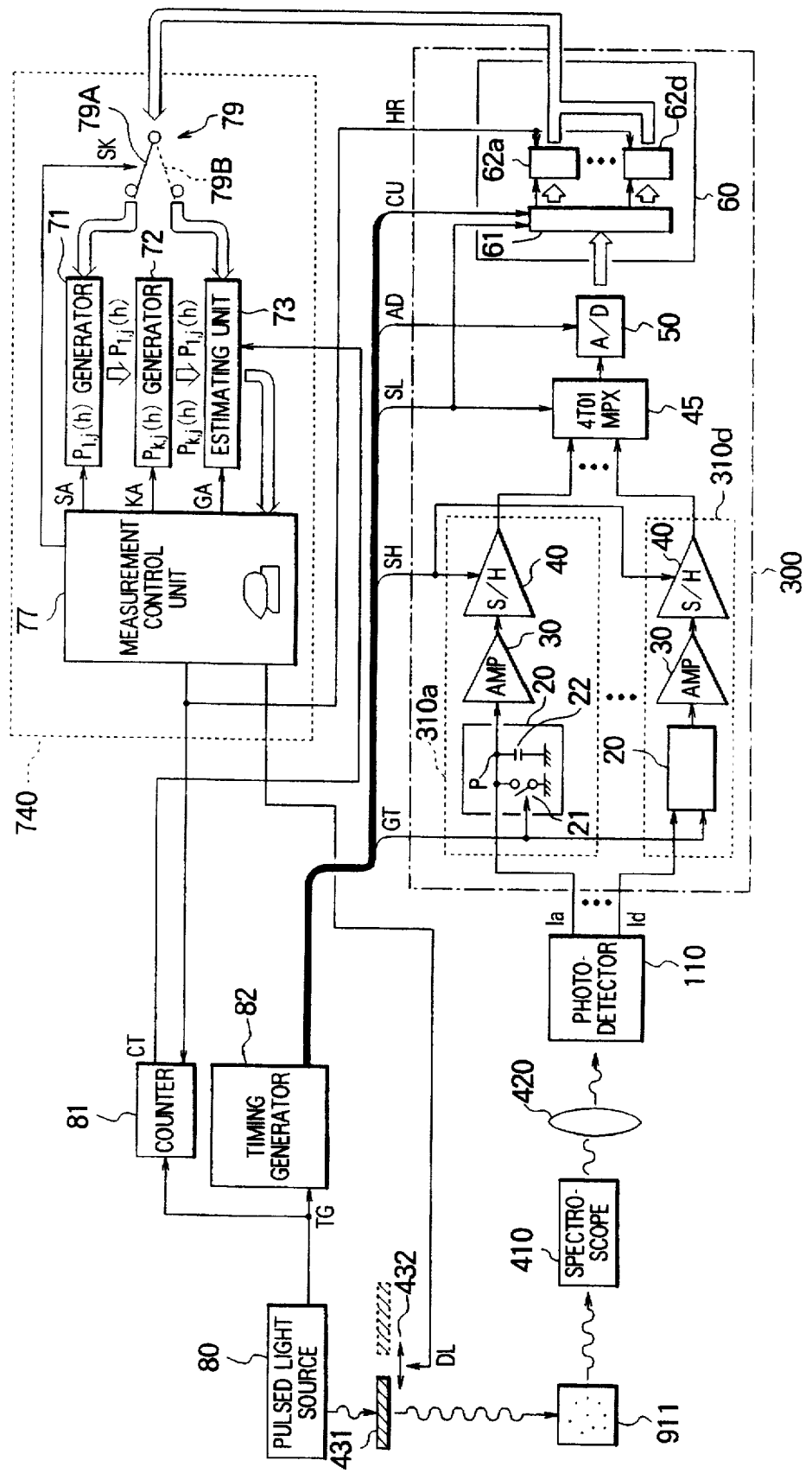
FIG. 15 is a structural drawing of a light measuring apparatus according to Embodiment 5 of the present invention.

FIG. 15 is a structural drawing of Embodiment 5 of the light measuring apparatus according to the present invention. The apparatus of the present embodiment is also different from Embodiment 3 in that measurement of the measurement-object light is carried out without a need for the calibration sample similarly as Embodiment 4. Because of this difference of function, the apparatus of the present embodiment is different from Embodiment 3 of FIG. 11 in that the apparatus further comprises (i) a light reducing filter 431 and (ii) a carrier 432 for moving the light reducing filter 431 in accordance with the light reducing instruction signal DL and in that the processing section 740 comprises a measurement control unit 77 for notifying the carrier 432 of the light reducing instruction signal DL, as shown in FIG. 15. Further, the apparatus of the present embodiment is different from Embodiment 4 in that the light reducing filter 431 is used not for reduction of the measurement-object light, but for reduction of the excitation light.

The apparatus of the present embodiment measures the intensity of the measurement-object light in the following manner.

Similarly as in Embodiment 3, the pulse height distributions for calibration, $p_{i,j}(h)(1 \leq i \leq k_{MAX})$, are generated prior to the measurement of the measurement-object light. For generating the pulse height distributions $p_{i,j}(h)$, the measurement control unit 77 makes the light reducing instruction signal DL significant to control the carrier 432 so as to locate the light reducing filter 431 on the optical path before the excitation pulsed light from the pulsed light source 80 is incident to the measurement object 911.

After that, the same operation as in Embodiment 3 is carried out to generate the pulse height distributions $p_{i,j}(h)$ $(1 \leq i \leq k_{MAX})$.

After the pulse height distributions $p_{i,j}(h)(1 \leq i \leq k_{MAX})$ are generated in this way, the measurement control unit 77 makes the light reducing instruction signal DL non-significant to control the carrier 432 so as to remove the light reducing filter 431 from the optical path before the excitation pulsed light from the pulsed light source 80 is incident to the measurement object 911, thereby letting the excitation light enter the measurement object 911.

After that, the same operation as in Embodiment 3 is carried out to estimate the photoelectron number distribution of photoelectrons occurring in each zone $13_j$ of the photoelectric conversion surface with incidence of the measurement-object light, thereby obtaining the intensity of the measurement-object light.

Figure 16:
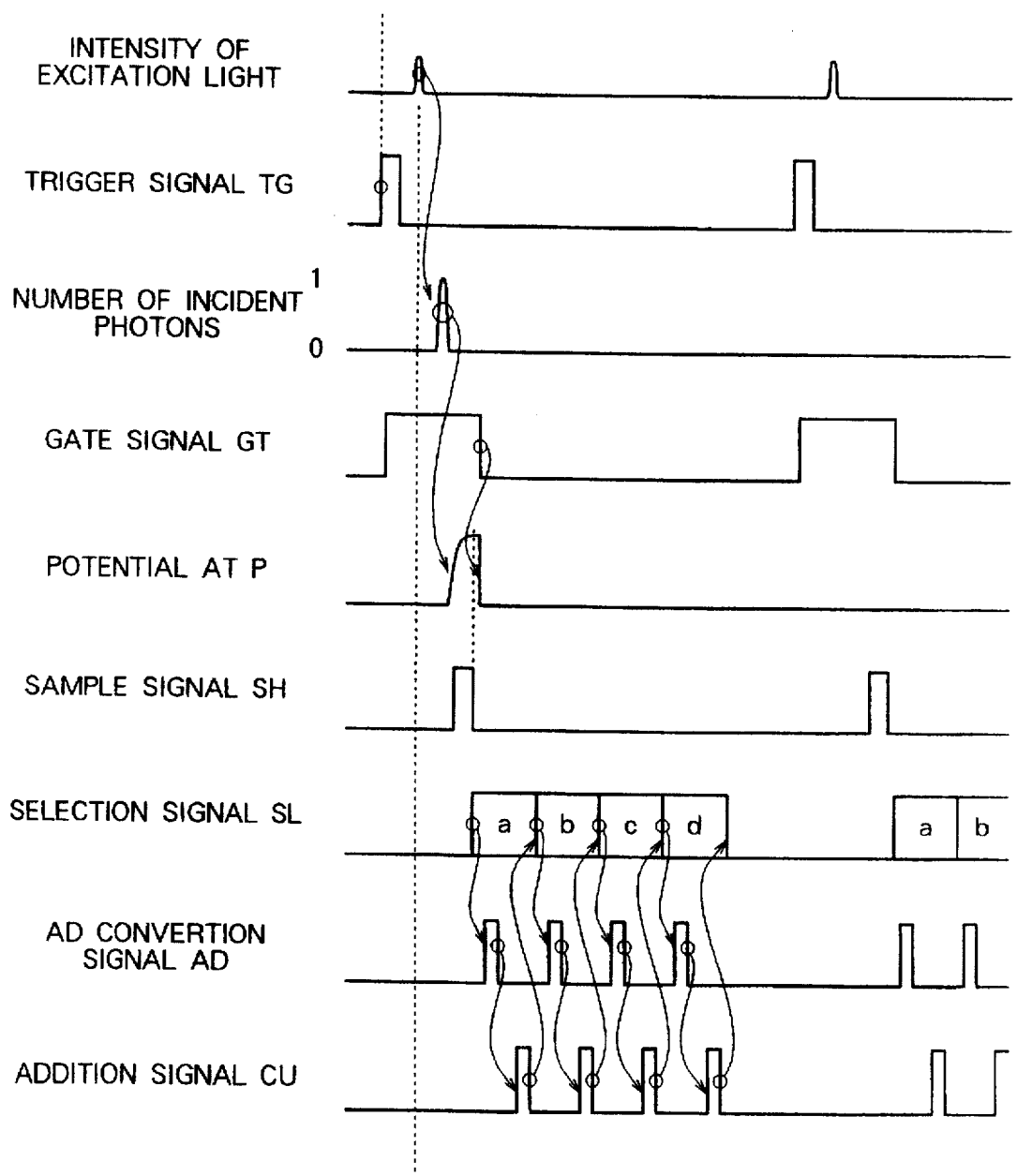
FIG. 16 is a timing chart to illustrate the operation upon collection of single photoelectron events in the light measuring apparatus of Embodiment 5.

FIG. 16 is a timing chart to illustrate the operation of from incidence of light to the photodetector 110 in the case of collection of single photoelectron events, to generation of the pulse height distributions $N_{1,j}(h)$ output from the collector 300. The timings shown in FIG. 16 are the same as those in FIG. 12, but they are shown herein in order to show states of decrease of the excitation light.

Since the quantity of irradiation light upon collection of single photoelectron events in the present embodiment can be smaller than that in Embodiment 4, the present embodiment can restrict change in properties of the measurement object due to bleaching or the like more than Embodiment 4.

(Embodiment 6)

Figure 17:
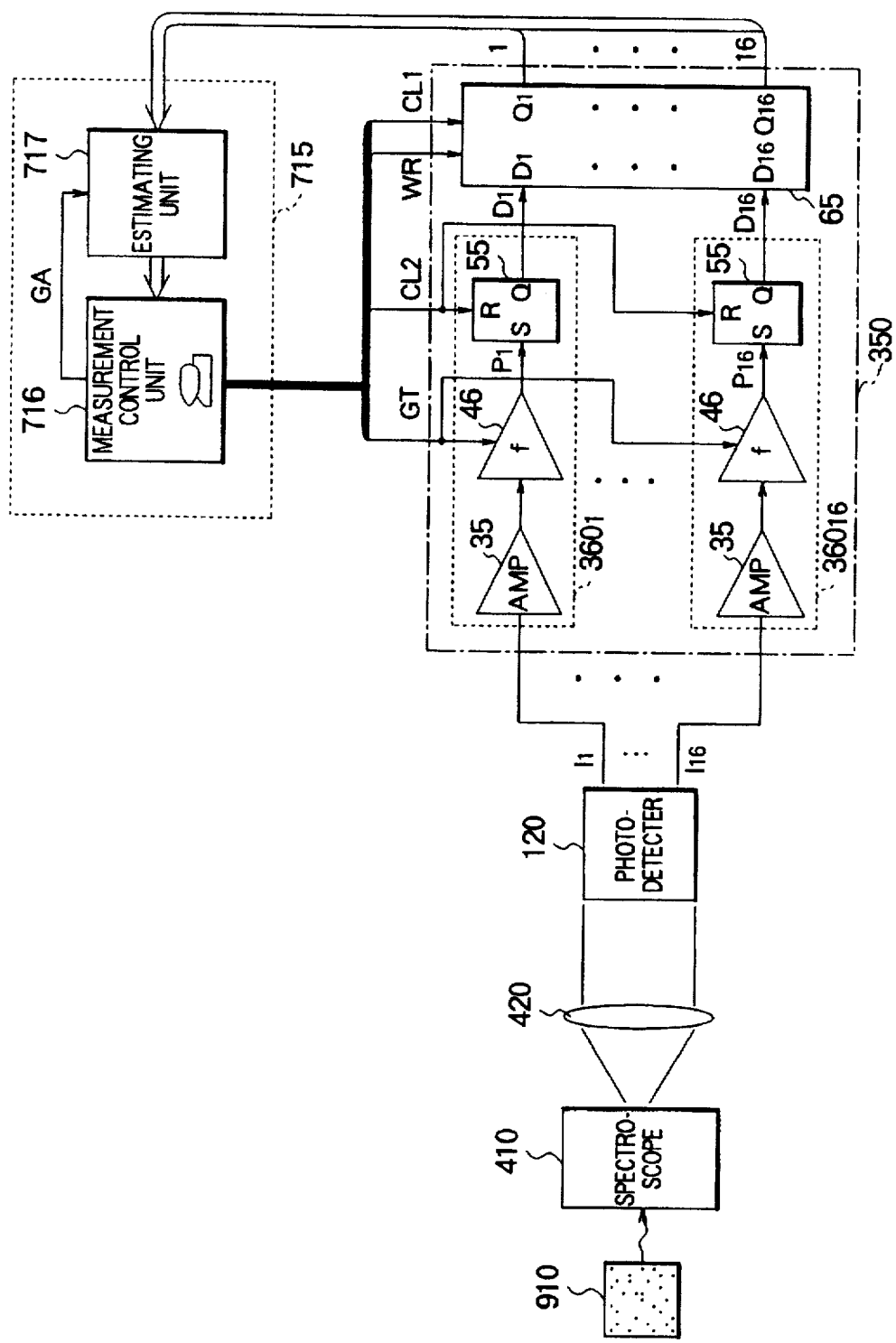
FIG. 17 is a structural drawing of a light measuring apparatus according to Embodiment 6 of the present invention.

FIG. 17 is a structural drawing of Embodiment 6 of the light measuring apparatus according to the present invention. As shown in FIG. 17, the apparatus of the present embodiment comprises (a) a spectroscope 410 for receiving spontaneously emitted light from the measurement object 910 and emitting light of wavelengths being a measurement object, (b) a photodetector 120 for receiving the measurement-object light emitted from the spectroscope 410 and coming through the optical system 420, emitting photoelectrons in the number according to a distribution of photoelectron numbers depending upon the number of photons of incident light, multiplying photoelectrons emitted from each of plural zones in the photoelectric conversion surface emitting the photoelectrons, and outputting pulse current signals $I_j$ (j=1 to 16) of every zone of the photoelectric conversion surface, (c) a collector 350 for determining pulse height values of pulse current signals $I_j$ within a gate period, and collecting and recording, for each zone of the photoelectric conversion surface, events in each of which the pulse height value of pulse current signal $I_j$ exceeds a predetermined value one or more times within the gate period, and (d) a processing section 715 for estimating a mean value of photoelectron generation numbers in the gate period for each zone of the photoelectric conversion surface, based on information of occurrence of events collected by the collector 350, thereby obtaining the intensity of the measurement-object light.

Figure 18:
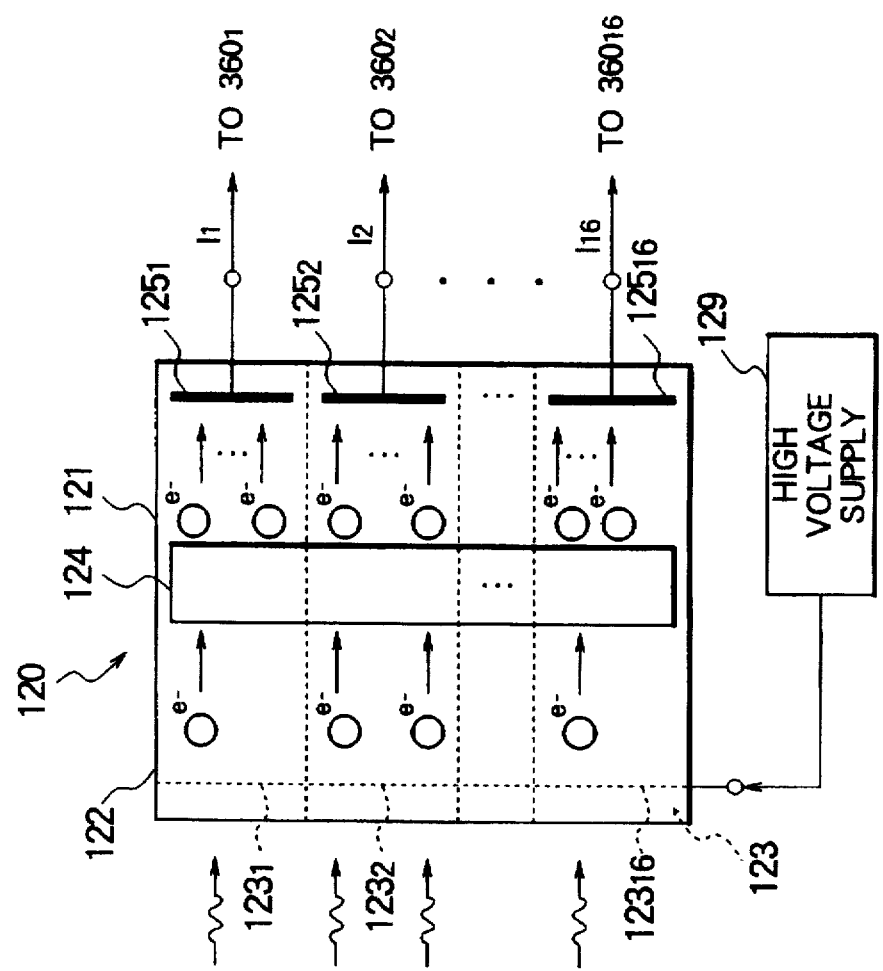
FIG. 18 a structural drawing of photodetector 120 in Embodiment 6.

FIG. 18 is a structural drawing of the photodetector 120. As shown in FIG. 18, the photodetector 120 comprises a photoelectric conversion surface 123 for emitting photoelectrons in the number according to the intensity of the measurement-object light incident thereto, an electron multiplier portion 124 for multiplying the photoelectrons to generate many secondary electrons, and a plurality of (16 herein) anode electrodes $125_{01}$ to $125_{16}$ for receiving the secondary electrons to output current pulse signals $I_1$ to $I_{16}$, arranged in a vacuum container 121 having an entrance window 122 for letting the measurement-object light pass. Here, the electron multiplier portion 124 may be multi-stage lattice-shaped dynodes as in a photomultiplier tube, or a microchannel plate. The sixteen anode electrodes $125_{01}$–$125_{16}$ are arranged in an array of 4×4 in a plane parallel to the photoelectric conversion surface 123. For simplicity, only three anode electrodes $15_{01}$, $15_{02}$, and $15_{16}$ are illustrated out of the sixteen anode electrodes.

In this photodetector 120, the photoelectric conversion surface 123 is kept at a lower potential than the anode electrodes $125_{01}$ to $125_{16}$; while a predetermined voltage is also applied to the electron multiplier portion 124, with incidence of the measurement-object light to the photoelectric conversion surface 123 the photoelectric conversion surface 123 emits photoelectrons in the number according to the intensity thereof; and then the photoelectrons are multiplied by the electron multiplier portion 124 to generate many secondary electrons. Then the secondary electrons reach either one of the anode electrodes $125_{01}$–$125_{16}$. An anode electrode $125_{01}$–$125_{16}$ outputting a current pulse signal upon arrival of the secondary electrons corresponds to a zone $123_{01}$–$123_{16}$ in which photons of the measurement-object light are incident to the photoelectric conversion surface 123.

The collector 350 comprises (i) event discriminating circuits $360_j$ provided for the respective zones $123_j$ of the photoelectric conversion surface, each outputting a significant event generation signal $D_j$ when a pulse height value of pulse current signal $I_j$ input thereto during the significant period of the gate signal GT becomes at least a predetermined value, and (ii) a buffer memory 65 for receiving the event generation signals $D_j$ in parallel and successively storing the event generation signals $D_j$ as digital signals of 16 bits in accordance with a write signal WR. The contents of the buffer memory 65 all are reset to 0 in accordance with an instruction of clear signal CL1.

Each event discriminating circuit $360_j$ comprises (i) an amplifier 35 for converting a pulse current signal $I_j$ input thereto into a voltage signal and amplifying it, (ii) a discriminator 46 for changing the level of output signal to significant when the pulse height value of pulse voltage signal input thereto exceeds the predetermined value during the significant period of the gate signal GT, and outputting a pulse voltage signal $P_j$, and (iii) an event holding circuit 55 for changing an output signal $D_j$ significant when the pulse voltage signal $P_j$ turns significant, and making the output signal $D_j$ non-significant in accordance with a clear signal CL2.

The processing section 715 comprises (i) an estimating unit 717 for receiving event occurrence data recorded in the collector 350 and estimating a mean value of photoelectron generation numbers in the gate period for each zone $123_j$ of the photoelectric conversion surface, based on the event occurrence data thus received, thereby obtaining the intensity of the measurement-object light, and (ii) a measurement control unit 716 for giving an instruction of activation of the estimating unit 717 and outputting the operation timing signals (GT, WR, CL1, CL2) to the collector 350.

Figure 19:
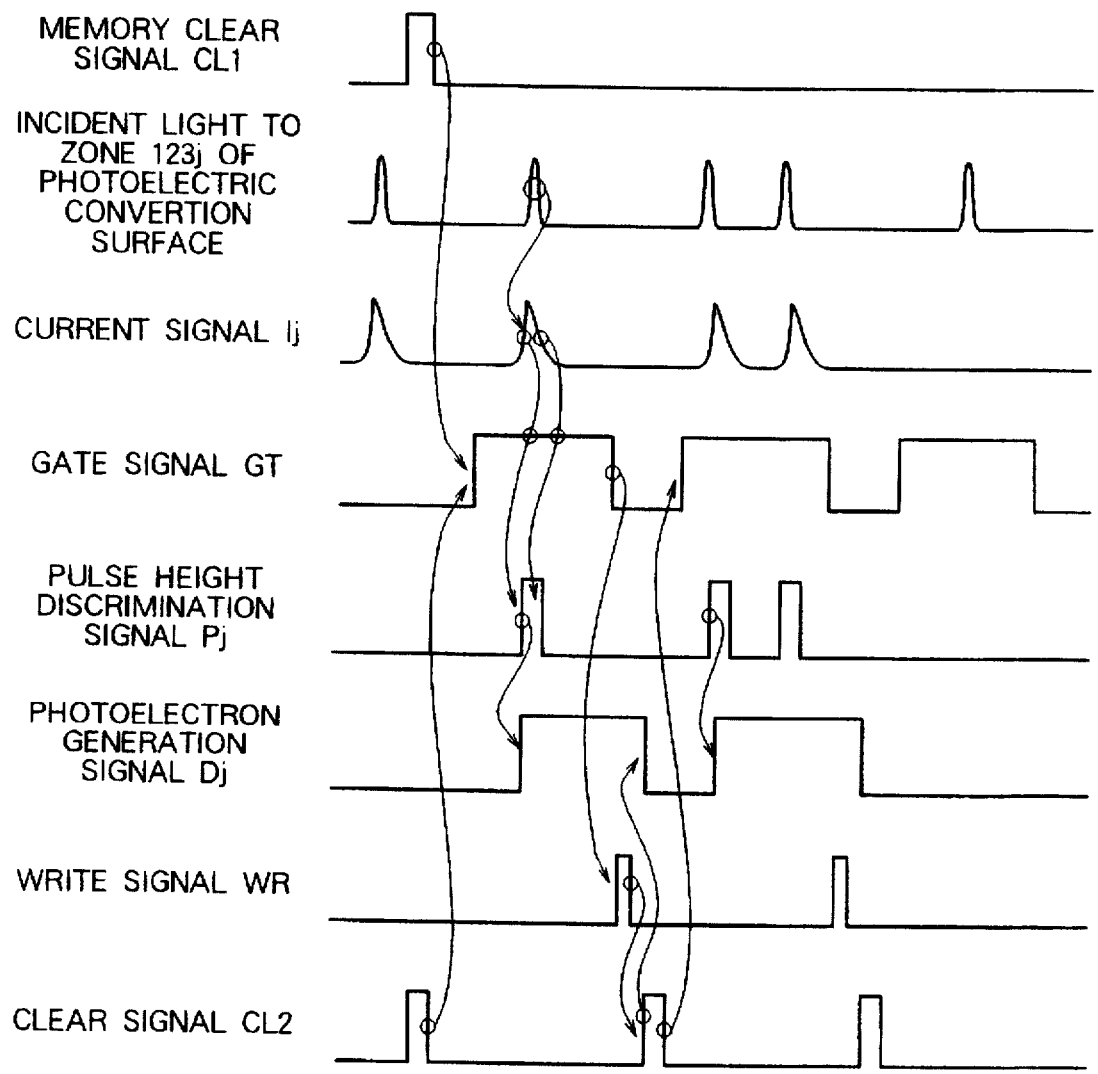
FIG. 19 is a timing chart to illustrate the operation upon measurement of measurement-object light in the light measuring apparatus of Embodiment 6.

The apparatus of the present embodiment measures the intensity of the measurement-object light in the following manner. FIG. 19 is a timing chart to illustrate the operation of from incidence of light to the photodetector 120, to recording of the event occurrence data $B_1(b_{1,1}, \ldots, b_{16,1})$ to $B_M (b_{1,M}, \ldots, b_{16,M})$ in the collector 350. Here, M indicates the number of occurrence of gate, m of $B_m$ 16-bit data at the m-th occurrence of gate, and $b_{j,m}$ presence or absence of occurrence of event according to each zone $123_j$ of the photoelectric conversion surface in the m-th gate period (1 for presence of event occurrence and 0 for absence of event occurrence).

The measurement control unit 716 first changes the clear signals CL1, CL2 temporarily significant to reset the all contents of the buffer memory 65 to the count value "0" and also reset the event holding circuits 55.

The light emitted from the measurement object 910 travels successively through the spectroscope 410 and optical system 420 to enter the photodetector 120.

In collection of one event, the measurement control unit 716 makes the gate signal GT, which is an integration instruction signal, significant over the time $T_G$. Current signals $I_j$ output from the photodetector 120 during the significant period of the gate signal GT are supplied to the event discriminating circuits $360_j$.

In each event discriminating circuit $360_j$ the amplifier 35 converts the current signal $I_j$ to a voltage signal and amplifies it to supply the amplified signal to the discriminator 46. The discriminator 46 compares the pulse voltage signal input thereto with a predetermined voltage value and makes the output signal $P_j$ significant when the input voltage signal value is not less than the predetermined voltage value, and it outputs the pulse voltage signal. When the pulse voltage signal $P_j$ is supplied to the event holding circuit 55, the output signal $D_j$ of the event holding circuit 55 becomes significant. Then the event holding circuit 55 holds to output the significant state of the event occurrence signal $D_j$ once having become significant.

Next, the measurement control unit 716 makes the write signal WR significant to write $(D_1, \ldots, D_{16})$ as 16-bit event occurrence data $B_1$ $(b_{1,1}, \ldots, b_{16,1})$ in the first gate period. After that, the measurement control unit 716 makes the clear signal CL2 temporarily significant to reset the event holding circuits 55.

After completion of the above operation of from making the gate signal GT significant to resetting the event hold circuits 55, the operation of from again changing the gate signal GT significant to resetting the event holding circuits 55 is repeated from the second time to the M-th time, thereby recording event occurrence information $B_m$ ($b_{j,m}$) in the buffer memory.

Then the measurement control unit 716 makes the activation instruction signal GA significant to activate the estimating unit 717. The estimating unit 717 thus activated receives the event occurrence information $B_m$ ($b_{j,m}$) from the buffer memory 65 in the collector 350 and performs the following arithmetic.

The number $n_k$ of current pulse signals, corresponding to at least one photoelectron, output from the anode electrode $125_k$ as to M pulses of gate signal is given as follows.

$$n_k = \sum_{m=1}^{M} b_{k,m} \tag{8}$$

Assuming that the from a zone photoelectrons emitted from a zone on the photoelectric conversion surface 123 corresponding to the anode electrode $125_k$ in a gate period given by the pulse width of the gate signal with incidence of the measurement-object light to the photoelectric conversion surface 123 is in accordance with the Poisson distribution, the mean photoelectron number thereof is referred to $\lambda_k$. Further, assuming that the number of photoelectrons emitted from the entire photoelectric conversion surface 123 in the gate period with incidence of the measurement-object light to the photoelectric conversion surface 123 is also in accordance with the Poisson distribution, the mean photoelectron number thereof is referred to as $\lambda$.

Under this assumption, the probability that no current pulse signal is output from the anode electrode $125_k$ in the gate period, that is, the probability $p_k(0)$ that no photoelectron is emitted from the zone $123_k$ on the photoelectric conversion surface 123 corresponding to the anode electrode $125_k$, is expressed as follows.

$$p_k(0) = \exp(-\lambda_k) \tag{9}$$

Therefore, the logarithmic likelihood where the number of times for the anode electrode $125_k$ to output at least one current pulse signal as to M pulses of gate signal is $n_k$ is given as follows.

$$\log L_k = (M - n_k) - \log\{p_k(0)\} + n_k - \log\{1 - p_k(0)\} \tag{10}$$
$$= -(M - n_k) - \lambda_k + n_k - \log\{1 - \exp(-\lambda_k)\}$$

The estimating unit 717 estimates the mean photoelectron number $\lambda$ by the maximum likelihood method based on this Eq. (10). Namely, the estimating unit 717 obtains the value $\lambda_k$ to maximize this logarithmic likelihood and makes such estimation that this value $\lambda_k$ is a mean value of photoelectrons emitted in the gate period from the zone $123_k$ on the photoelectric conversion surface 123 corresponding to the anode electrode $125_k$ when the measurement-object light is incident to the photoelectric conversion surface 123. The value $\lambda_k$ to maximize the logarithmic likelihood given by Eq. (10) is given as follows by differentiating Eq. (10) by $\lambda_k$ and setting it to 0.

$$\lambda_k = -\log(1 - n_k/M) \tag{11}$$

The estimating unit 717 further obtains by the following equation the mean photoelectron number $\lambda$ of photoelectrons emitted in the gate period from the entire photoelectric conversion surface 123 with incidence of the measurement-object light to the photoelectric conversion surface 123, and obtains the intensity of the measurement-object light received by the photodetector 120, based on this mean photoelectron number $\lambda$.

$$\lambda = \sum_{k=1}^{16} \lambda_k \tag{12}$$

Next described are results of simulation calculation having been conducted as to the estimation precision of the mean photoelectron number $\lambda$ in the light measuring apparatus according to the present embodiment. Conditions of simulation calculation were as follows. The number of anode electrodes was set to 1, 4, or 16, and the mean photoelectron number $\lambda$ of photoelectrons emitted in the gate period from the photoelectric conversion surface 123 was 0.06, 0.1, 0.2, 0.3, 0.6, 1, 2, 3, 6, 10, or 20. For all combinations of the above conditions, the pulse number M of gate signal was set to 10000 and simulation calculation was carried out 500 times to estimate the mean photoelectron number $\lambda$. The standard deviation of the 500 mean photoelectron numbers $\lambda$ thus estimated was taken as estimation precision. For this simulation calculation, such assumption was made that secondary electrons generated when the photoelectrons emitted from the photoelectric conversion surface 123 entered the electron multiplier portion 124 were incident evenly to each of the four or sixteen anode electrodes.

Figure 20:
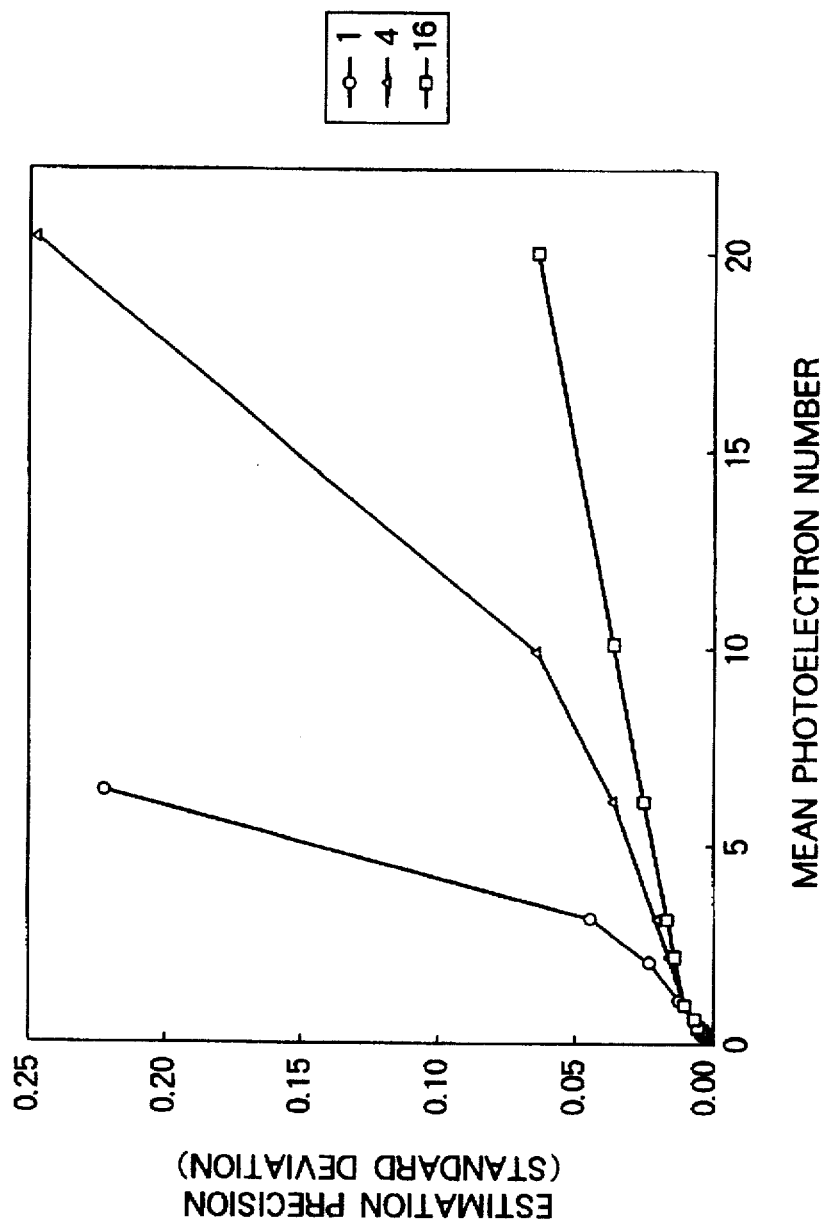
FIG. 20 is a graph to show simulation calculation results of estimation precision of mean photoelectron number for the light measuring apparatus of Embodiment 6.

FIG. 20 is a drawing to show the simulation calculation results of the estimation precision of mean photoelectron number in the light measuring apparatus according to the present embodiment. In this figure, each mark ○ represents estimation precision (standard deviation) in the case of a single anode electrode, each mark △ estimation precision (standard deviation) in the case of four anode electrodes, and each mark □ estimation precision (standard deviation) in the case of sixteen anode electrodes, respectively. As seen from FIG. 20, the greater the number of anode electrodes for detecting the photoelectrons emitted from the photoelectric conversion surface 123, the higher the precision of estimating the mean photoelectron number $\lambda$. Especially, in the range where the mean photoelectron number $\lambda$ is over 1, the estimation precision of mean photoelectron number $\lambda$ varies greatly depending upon the number of anode electrodes. In the case of one anode electrode, estimation becomes impossible if the mean photoelectron number $\lambda$ is over 6. In the case of the sixteen anode electrodes, the estimation precision (standard deviation) was still good, 0.064, even if the mean photoelectron number $\lambda$ was 20.

If a spectrum is measured as described above, the mean photoelectron number can be estimated as processing the current pulse signals each output from the plural anode electrodes in parallel, which expands the range of intensity of incident light that can be detected at high precision. Therefore, the spectrum can be measured with accuracy even if there is a great difference between peak intensities of the spectrum of the measurement-object light.

(Embodiment 7)

Figure 21:
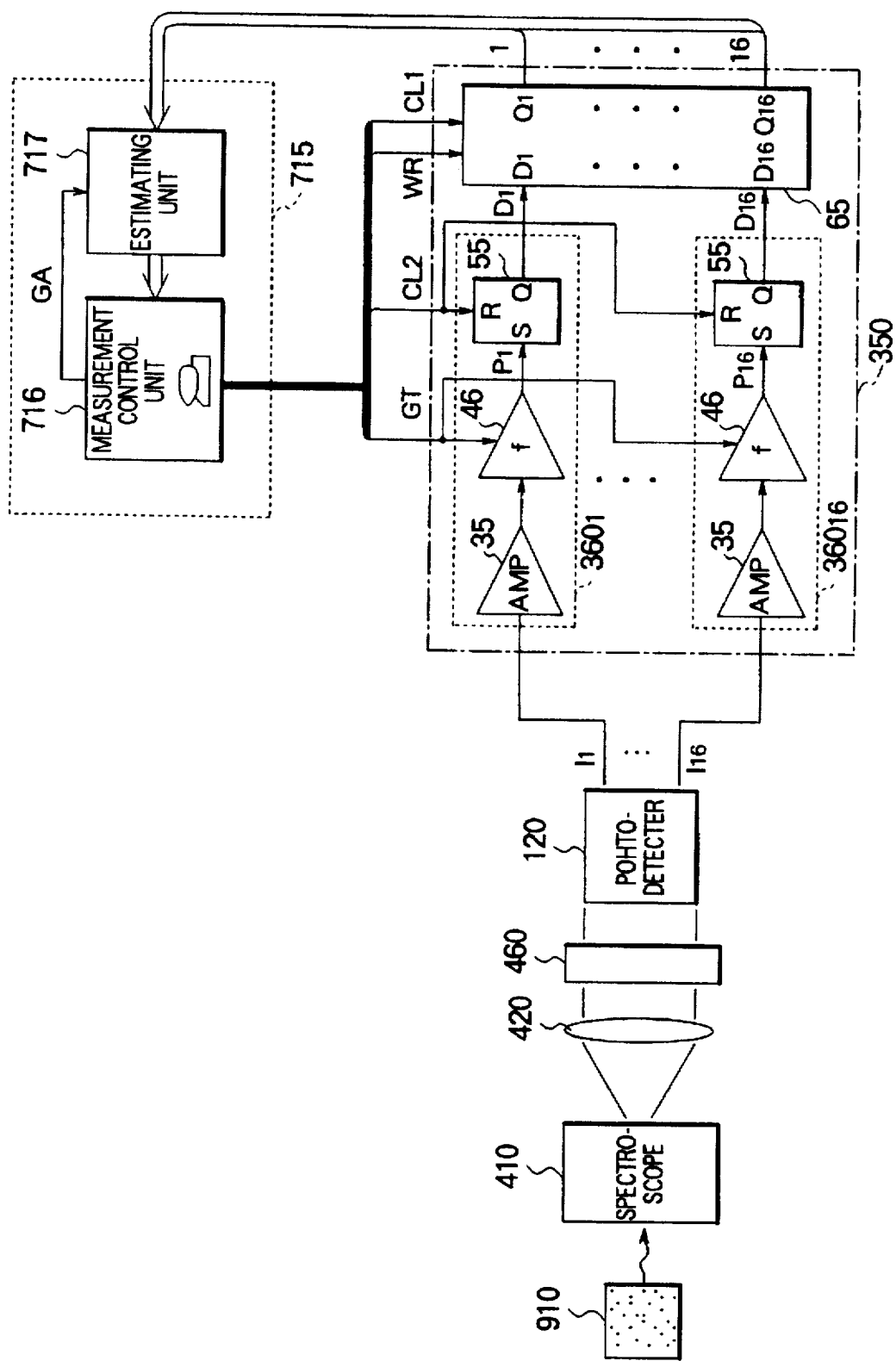
FIG. 21 is a structural drawing of a light measuring apparatus according to Embodiment 7 of the present invention.

FIG. 21 is a structural drawing of Embodiment 7 of the light measuring apparatus according to the present invention. As shown in FIG. 21, the apparatus of the present embodiment is different from that of Embodiment 6 in that it further comprises a homogenizing optical system 460 between the optical system 420 and the photodetector 120.

FIGS. 22 and 23 are explanatory drawings of the homogenizing optical system 460. FIG. 22 is a structural drawing of the homogenizing optical system 460 and FIG. 23 is a drawing to show a profile of the measurement-object light incident onto the photoelectric conversion surface 123 of the photodetector 120 through the homogenizing optical system 460. The homogenizing optical system 460 comprises two reflectors 461A and 461B arranged at a certain angle and in contact with each other at their one sides and receiving the measurement-object light, a reflector 462 for reflecting part of the measurement-object light reflected by the reflector 461A toward the photoelectric conversion surface 123, and a reflector 463 for reflecting the rest of the measurement-object light reflected by the reflector 461B toward the photoelectric conversion surface 123 of the photodetector 120.

In Embodiment 6, the measurement-object light output from the spectroscope 410 travels through the optical system 420 to enter the photoelectric conversion surface 123 of the photodetector 120. In this case, normally, the measurement-object light incident to the photoelectric conversion surface 123 is high in intensity near the beam center but weak in the periphery. Therefore, frequencies of incidence of secondary electrons to specific anode electrodes out of the plural anode electrodes in the photodetector 120 become higher, which degrades the estimation precision of mean photoelectron number for the specific anode electrodes. This also degrades the estimation precision of the mean value of numbers of photoelectrons emitted from the photoelectron conversion surface 123 of the photodetector 120.

In the apparatus of the present embodiment, when the measurement-object light of a circular shape having such a profile that intensities become stronger with approaching the center is incident uniformly to the reflectors 461A and 461B of the homogenizing optical system 460, a half (a semicircular shape) of the measurement-object light is reflected by the reflector 461A and reflector 462 in order, and the rest half is reflected by the reflector 461B and reflector 463 in order, thereby entering the photoelectric conversion surface 123 of photodetector 120 as superimposed on each other. The profile of the measurement-object light incident onto the photoelectric conversion surface 123 is as shown in FIG. 23, where the center portions (the portions of high intensities) of the measurement-object light are superimposed on the peripheral portions (the portions of weak intensities), whereby uniformity of the measurement-object light incident to the photoelectric conversion surface 123 can be improved. Accordingly, the frequencies of the secondary electrons reaching the plural anode electrodes of photodetector 120 also become uniform, which improves the estimation precision of mean photoelectron number $\lambda$, that is, the intensity measurement precision of the measurement-object light.

(Embodiment 8)

Figure 24:
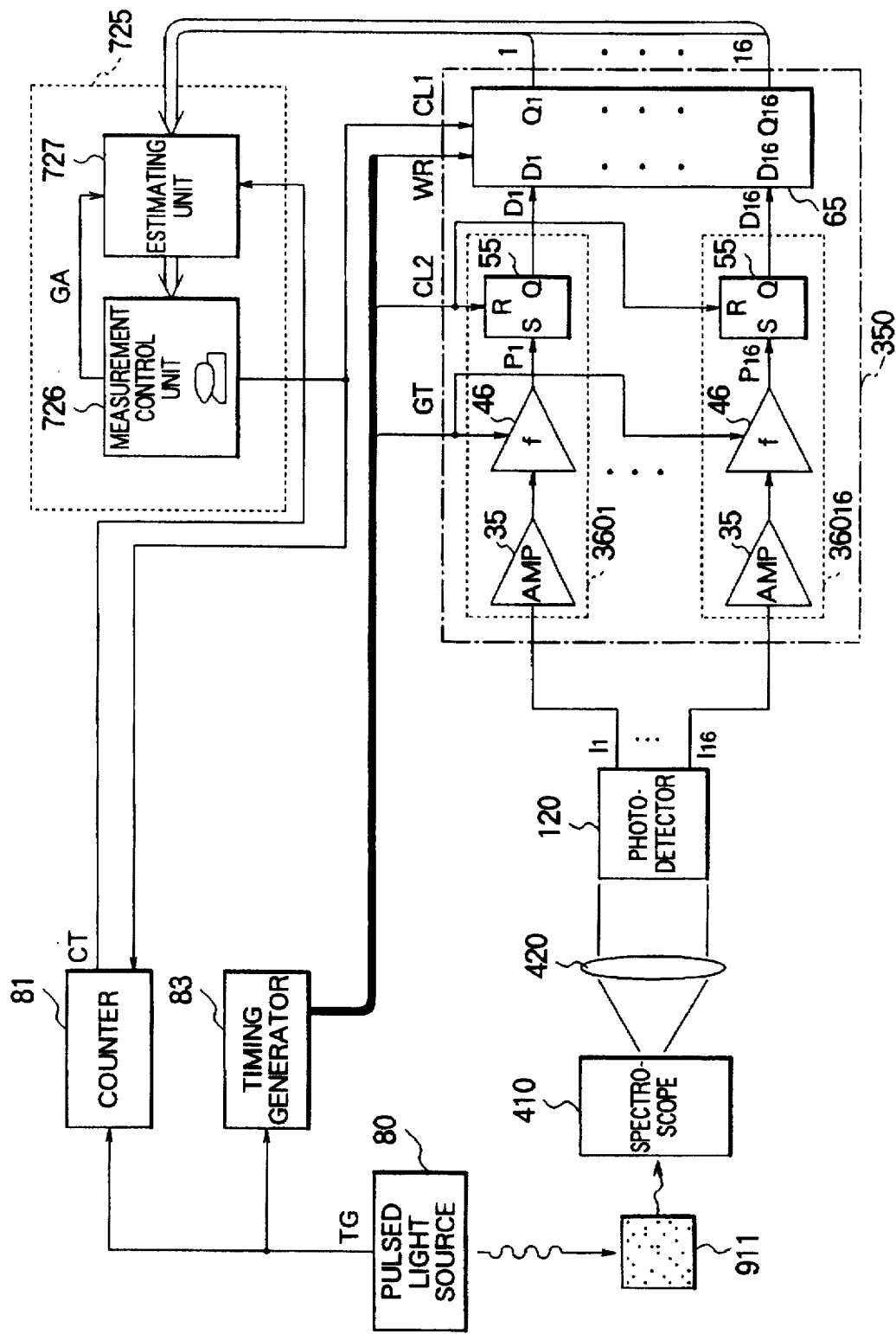
FIG. 24 is a structural drawing of a light measuring apparatus according to Embodiment 8 of the present invention.

FIG. 24 is a structural drawing of Embodiment 8 of the light measuring apparatus according to the present invention. The apparatus of the present embodiment is characterized in that the measurement object generates fluorescence not spontaneously but by irradiation of excitation light. Then the apparatus measures the fluorescence as measurement-object light.

As shown in FIG. 24, the apparatus of the present embodiment comprises (a) a spectroscope 410 for receiving the fluorescence from the measured object 911, generated upon irradiation with excitation light, separating it, and emitting light of wavelengths becoming a measurement object, (b) a photodetector 120 for receiving the measurement-object light emitted from the spectroscope 410 and coming through the optical system 420, emitting photoelectrons in the number according to a distribution of photoelectron numbers depending upon the number of photons of incident light, multiplying photoelectrons emitted from each of plural zones in the photoelectric conversion surface emitting the photoelectrons, and outputting pulse current signals $I_j$ (j=1 to 16) of every zone of the photoelectric conversion surface, (c) a collector 350 for determining pulse height values of pulse current signals $I_j$ within the gate period, and collecting and recording, for each zone of the photoelectric conversion surface, events in each of which the pulse height value of pulse current signal $I_j$ exceeds a predetermined value one or more times within the gate period, (d) a pulsed light source 80 for outputting excitation pulsed light and a generation timing signal TG of the pulsed light, (e) a counter 81 for receiving the generation timing signal TG and counting the number of generation times of the pulsed light of the pulsed light source 80, (f) a timing generating circuit 83 for receiving the generation timing signal TG and outputting the operation timing signals (GT, WR, CL2) to the collector 350, and (g) a processing section 725 for estimating a mean value of photoelectron generation numbers in the gate period for each zone of the photoelectric conversion surface, based on information of occurrence of events collected by the collector 350, thereby obtaining the intensity of the measurement-object light.

The processing section 725 comprises (i) an estimating unit 727 for receiving the event occurrence data recorded in the collector 350 and estimating the mean value of photoelectron occurrence numbers in the gate period for each zone $123_j$ of the photoelectric conversion surface, based on the event occurrence data thus received, thereby obtaining the intensity of the measurement-object light, and (ii) a measurement control unit 726 for giving an instruction of activation of the estimating unit 727 and outputting the clear signal CL1 to the collector 350 and to the counter 81.

Figure 25:
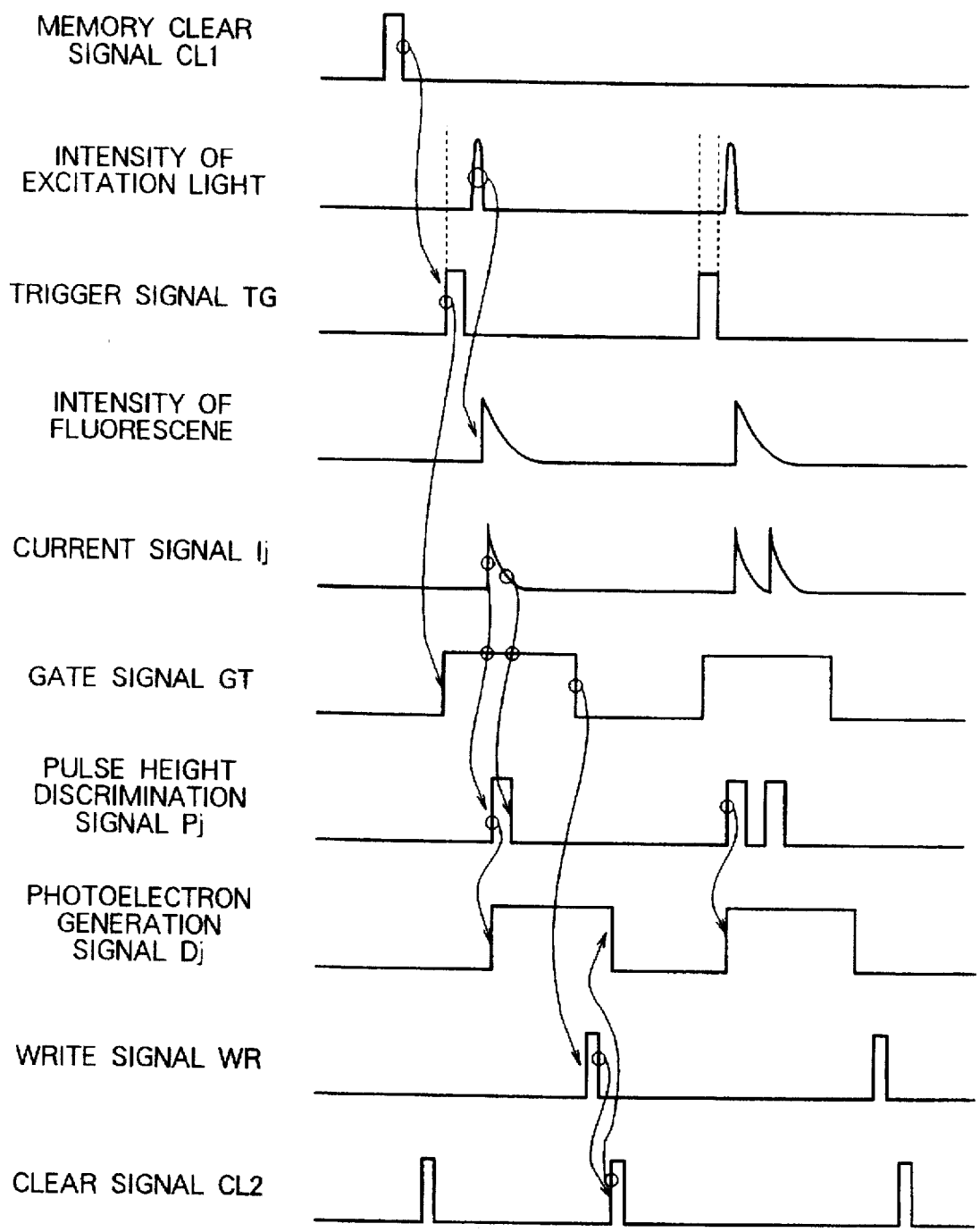
FIG. 25 is a timing chart to illustrate the operation upon measurement of measurement-object light in the light measuring apparatus of Embodiment 8.

The apparatus of the present embodiment measures the intensity of the measurement-object light in the following manner. FIG. 25 is a timing chart to illustrate the operation of from incidence of light to the photodetector 120, to recording of the event occurrence data $B_m$ ($b_{j,m}$) in the collector 350.

First, the measurement control unit 716 makes the clear signal CL1 temporarily significant and the timing generating circuit 83 makes the clear signal CL2 temporarily significant, thereby resetting the all contents of the buffer memory 65 and the counter 81 to the count value "0" and also resetting the event holding circuits 55. Then the pulsed light source 80 regularly emits the excitation pulsed light, and the timing signal TG a little earlier than emission of the excitation pulsed light.

Receiving the timing signal TG, the timing generating circuit 83 turns the gate signal GT significant to await arrival of the incident light to the photodetector 120.

Fluorescence generated by irradiation of the calibration sample 921 after the excitation pulsed light is emitted from the pulsed light source 80 is incident through the spectroscope 410 and optical system 420 in order, to the photodetector 120.

The current signals $I_j$ output from the photodetector 120 during the significant period of the gate signal GT are input into the event discriminating circuits $360_j$.

In each event discriminating circuit $360_j$ the amplifier 35 converts the current signal $I_j$ to a voltage signal and amplifies it to supply the amplified signal to the discriminator 46.

The discriminator 46 compares the pulse voltage signal input thereto with a predetermined voltage value and makes the output signal $P_j$ significant when the input voltage signal value is not less than the predetermined voltage value, and it outputs a pulse voltage signal. When the pulse voltage signal $P_j$ is supplied to the event holding circuit 55, the output signal $D_j$ of the event holding circuit 55 becomes significant. Then the event holding circuit 55 holds to output the significant state of the event occurrence signal $D_j$ once having become significant.

Next, the timing generating circuit 83 makes the write signal WR significant to write $(D_1, \ldots, D_{16})$ as 16-bit event occurrence data $B_1(b_{1,1}, \ldots, b_{16,1})$ in the first gate period. After that, the timing generating circuit 83 makes the clear signal CL2 temporarily significant to reset the event holding circuits 55.

After completion of the above operation of from making the gate signal GT significant to resetting the event holding circuits 55, the operation of from again changing the gate signal GT significant to resetting the event holding circuits 55 is repeated from the second time to the M-th time, thereby recording event occurrence information $B_m$ ($b_{j,m}$) in the buffer memory.

Then the measurement control unit 726 makes the activation instruction signal GA significant to activate the estimating unit 727. The estimating unit 727 thus activated receives the event occurrence data recorded in the collector 350 and estimates the mean value of photoelectron occurrence numbers in the gate period for each zone $123_j$ of the photoelectric conversion surface, based on the event occurrence data thus received, thereby obtaining the intensity of the measurement-object light, similarly as in Embodiment 7.

(Embodiment 9)

Figure 26:
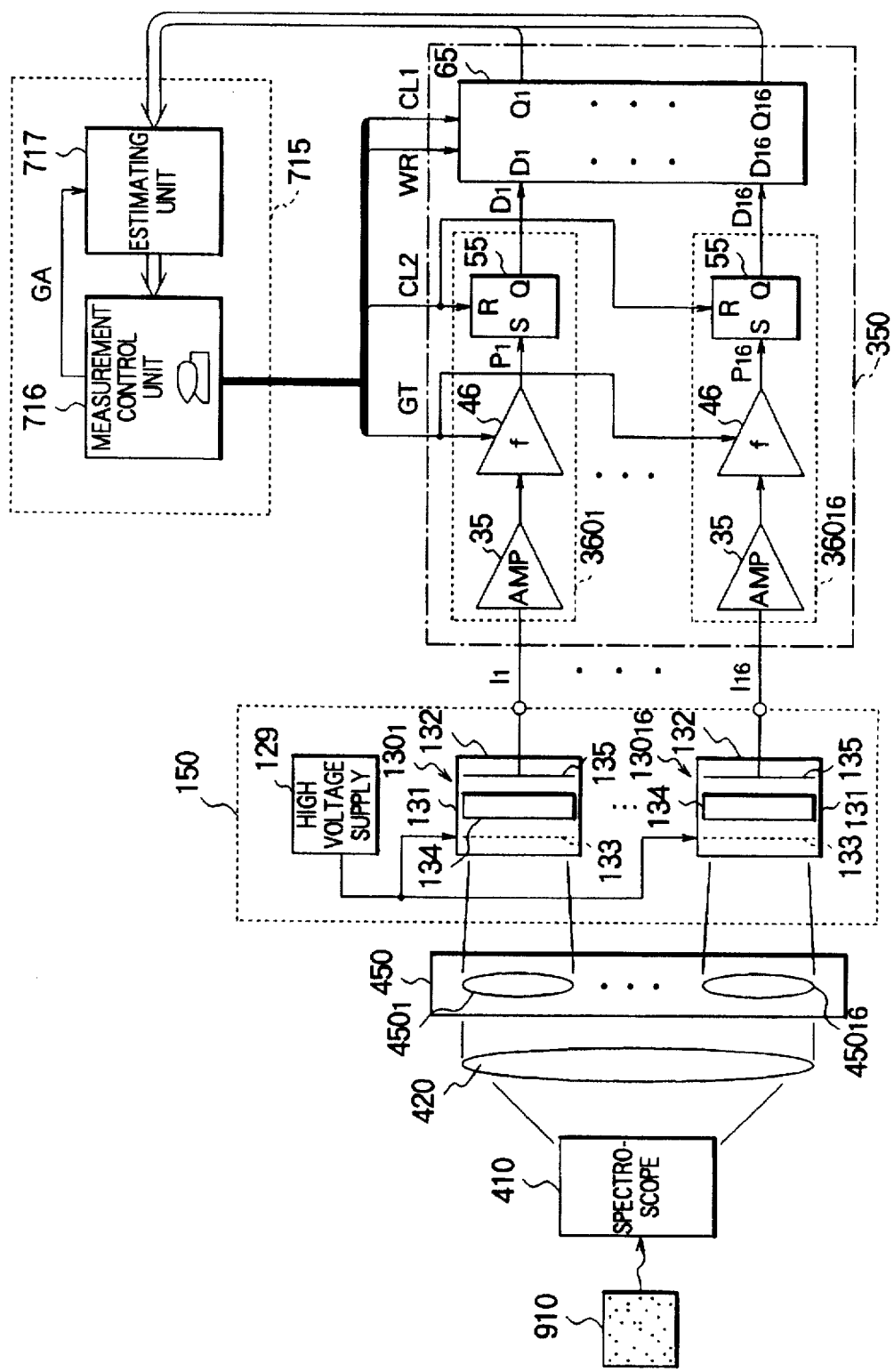
FIG. 26 is a structural drawing of a light measuring apparatus according to Embodiment 9 of the present invention.

FIG. 26 is a structural drawing of Embodiment 8 of the light measuring apparatus according to the present invention. The apparatus of the present embodiment is different from Embodiment 6 in that it uses a photodetection section 150 comprising photodetectors $130_1-130_{16}$ instead of the photodetector 120 in Embodiment 6 and in that it further comprises a lens array 450 in which lenses $450_1$ to $450_{16}$, which compose a dividing optical system disposed between the optical system 420 and a light receiving surface of the photodetection section 150, are arrayed corresponding to the photodetectors $130_1$ to $130_{16}$.

The photodetection section comprises (i) photodetectors $130_1$ to $130_{16}$ and (ii) a high-voltage supply 129 for applying a high voltage to the photodetectors $130_1$ to $130_{16}$.

Each photodetector $130_1$ comprises a photoelectric conversion surface 133 for emitting photoelectrons in the number according to the intensity of incident light, an electron multiplier portion 134 for multiplying the photoelectrons to generate many secondary electrons, and an anode electrode 135 for receiving the secondary electrons to output a current pulse signal $I_j$, which are arranged in a vacuum vessel 131 having an entrance window 132 for letting the measurement-object light pass.

In the apparatus of the present embodiment, the measurement-object light from the measurement object 910 travels successively through the spectroscope 410, optical system 420, and lenses $450_j$ to enter the photodetectors $130_j$. Then the photodetectors $130_j$ output current pulse signals $I_j$, and the current pulse signals $I_j$ are supplied to the collector 350.

After that, the apparatus operates in the same manner as in Embodiment 6, so that the event occurrence data recorded in the collector 350 is supplied to the estimating unit, which estimates the mean value of photoelectron occurrence numbers in the gate period for each zone $123_j$ of the photoelectric conversion surface, based on the event occurrence data thus received, thereby obtaining the intensity of the measurement-object light.

From the invention thus described, it will be obvious that the invention may be varied in many ways. Such variations are not to be regarded as a departure from the spirit and scope of the invention, and all such modifications as would be obvious to one skilled in the art are intended to be included within the scope of the following claims.

The basic Japanese Application Nos. 330482/1995 filed on Dec. 19, 1995 and 251787/1996 filed on Sep. 24, 1996 are hereby incorporated by reference.

What is claimed is:

1. A light measuring apparatus comprising:

photodetection means having a photoelectric conversion surface for emitting photoelectrons in a number according to a photodetection number distribution depending upon a number of photons of incident light, and a plurality of electron multiplier portions provided corresponding to a plurality of zones of said photoelectric conversion surface, each electron multiplier portion multiplying photoelectrons emitted from an associated zone of said photoelectric conversion surface to output a current signal as to said associated zone;

collecting means for collecting photoelectron occurrence events in the respective zones of said photoelectric conversion surface in a gate period, based on current signals output from said respective electron multiplier portions; and estimating means for estimating a distribution of numbers of photoelectrons emitted with incidence of measurement-object light in each zone of said photoelectric conversion surface in said gate period, based on collection results by said event collecting means, and thereby obtaining an intensity of the measurement-object light.

2. The light measuring apparatus according to claim 1, wherein said photodetection means comprises a photodetector;

said photodetector comprising:
a photoelectric conversion surface for emitting photoelectrons in a number according to a photon number distribution of incident light in each of plural zones;
a plurality of electron multiplier portions, each multiplying photoelectrons emitted from an associated zone of said photoelectric conversion surface to output a current signal as to said associated zone; and
a vacuum vessel having a transmissive window for letting the incident light pass and enclosing said photoelectric conversion surface and said electron multiplier portions therein.

3. The light measuring apparatus according to claim 1, wherein said collecting means comprises:

integrating means provided for each of said electron multiplier portions, each integrating means integrating said current signal output from each said electron multiplier portion to convert said current signal to a voltage signal and outputting said voltage signal as a pulse height value of one event; and first generating means for collecting pulse height values for every event as to each said electron multiplier portion and generating pulse height distributions ($N_j$(h); h is pulse height values) of number of event against pulse height value; and wherein said estimating means comprises:
second generating means for generating a pulse height distribution of single photoelectron events $(p_{1,j}(h))$, based on the pulse height distribution $(N_{1,j}(h))$ generated by said first generating means, for each said electron multiplier portion in the case of setting in a collection mode of single photoelectron events in each of which a number of photoelectrons emitted in said photodetection means is substantially at most one;

third generating means for recursively calculating values as defined below, for each said electron multiplier portion, based on said pulse height distribution of single photoelectron events $(p_{1,j}(h))$, $$p_{k,j}(h) = \int_0^h (p_{k-1,j}(l) - p_{1,j}(h-l))dl \quad (1)$$

and thereby generating pulse height distributions of k-photoelectron events $(p_{k,j}(h))$ in each of which a number of photoelectrons emitted from said photodetection means is k ($2 \leq k \leq k_{MAX}$), for each zone of said photoelectric conversion surface; and photoelectron number distribution estimating means for estimating said photoelectron number distribution for a case wherein the measurement-object light is incident to said photodetection means, based on pulse height distributions $(N_j(h))$ generated by said first generating means when said measurement-object light is incident to said photodetection means in the case of setting in a normal measurement mode, said pulse height distributions of single photoelectron events already obtained $(p_{1,j}(h))$, and said pulse height distributions of k-photoelectron events already obtained $(p_{k,j}(h))$, thereby obtaining the intensity of said measurement-object light.

4. The light measuring apparatus according to claim 3, wherein each of the electron multiplier portions of said photodetection means comprises an avalanche photodiode, between an anode and a cathode of which a reverse bias voltage is applied and a portion of which opposed to said photoelectric conversion surface is set at a higher potential than a potential of said photoelectric conversion surface, for avalanche-multiplying electron-hole pairs generated with incidence of said photoelectrons and outputting said current signal according to a number of electron-hole pairs thus avalanche-multiplied.

5. The light measuring apparatus according to claim 3, wherein said first generating means comprises:
an analog-to-digital converter for receiving said voltage signal every event, converting said voltage signal to a digital value, and outputting the digital signal as a pulse height value; and
event counting means for counting and storing a number of events occurring, for each digital value output from said analog-to-digital converter, and
wherein said third generating means calculates values defined below to obtain pulse height distributions of single photoelectron events $(p_{k,j}(h))$, $$p_{k,j}(h) = \sum_{l=0}^{h} (p_{k-1,j}(l) - p_{1,j}(h-l)). \quad (2)$$

6. The light measuring apparatus according to claim 3, wherein said estimating means estimates said photoelectron number distribution by the maximum likelihood method.

7. The light measuring apparatus according to claim 3, wherein said estimating means estimates said photoelectron number distribution under such an assumption that said photoelectron number distribution is a Poisson distribution.

8. The light measuring apparatus according to claim 3, further comprising light reducing means for reducing a quantity of light incident to said photodetection means in reply to a case of setting in the collection mode of single photoelectron events.

9. The light measuring apparatus according to claim 8, wherein said light reducing means comprises a light reducing filter for reducing the intensity of light incident thereto and outputting the light toward said photodetection means.

10. The light measuring apparatus according to claim 3, further comprising:
a pulsed light source for outputting pulsed light for irradiating a measurement object and also outputting a generation timing signal of said pulsed light;
operation timing signal generating means for generating an integration instruction signal and a collection instruction signal from said generation timing signal of the pulsed light and for sending said integration instruction signal to said integrating means and said collection instruction signal to said first generating means; and
a counter for counting a number of generation times of said pulsed light from the generation timing signal of said pulsed light.

11. The light measuring apparatus according to claim 10, further comprising light reducing means for reducing a quantity of light incident to said photodetection means in reply to a case of setting in the collection mode of single photoelectron events.

12. The light measuring apparatus according to claim 11, wherein said light reducing means comprises a light reducing filter for receiving the measurement-object light from a measurement object, reducing the intensity of the light, and outputting the light toward said photodetection means.

13. The light measuring apparatus according to claim 11, wherein said light reducing means comprises a light reducing filter for receiving the pulsed light output from said pulsed light source, reducing the intensity of the light, and outputting the light toward the measurement object.

14. The light measuring apparatus according to claim 3, further comprising measurement control means for giving an instruction of activation of said second generating means in the case of setting in the collection mode of single photoelectron events and giving an instruction of activation of said photoelectron number distribution estimating means in the case of setting in the normal measurement mode.

15. The light measuring apparatus according to claim 14, wherein said measurement control means sends an integration instruction signal to said integrating means and sends a collection instruction signal to said first generating means.

16. The light measuring apparatus according to claim 14, further comprising light reducing means for reducing a quantity of light incident to said photodetection means for a case wherein a single photoelectron event instruction signal is significant to effect setting in the collection mode of single photoelectron events, wherein said measurement control means outputs said single photoelectron event instruction signal.

17. The light measuring apparatus according to claim 16, wherein said light reducing means comprises:
a light reducing filter for reducing the intensity of light incident thereto and outputting the light toward said photodetection means; and
carrying means for locating said light reducing filter at a position where the light to enter said photodetection means passes, when said single photoelectron event instruction signal is significant, and locating said light reducing filter at a position where the light to enter said photodetection means does not pass, when said single photoelectron event instruction signal is non-significant.

18. The light measuring apparatus according to claim 14, further comprising:

a pulsed light source for outputting pulsed light for irradiating a measurement object and also outputting a generation timing signal of said pulsed light;

operation timing signal generating means for generating said integration instruction signal and said collection instruction signal from said generation timing signal of the pulsed light and for sending said integration instruction signal to said integrating means and said collection instruction signal to said first generating means;

a counter for counting a number of generation times of said pulsed light from the generation timing signal of said pulsed light; and light reducing means for reducing a quantity of light incident to said photodetection means for a case wherein a single photoelectron event instruction signal is significant to effect setting in the collection mode of single photoelectron events, wherein said measurement control means outputs said single photoelectron event instruction signal.

19. The light measuring apparatus according to claim 18, wherein said light reducing means comprises:

a light reducing filter for receiving the measurement-object light from the measurement object, reducing the intensity of the light, and outputting the light toward said photodetection means; and carrying means for locating said light reducing filter at a position where the light to enter said photodetection means passes, when said single photoelectron event instruction signal is significant, and locating said light reducing filter at a position where the light to enter said photodetection means does not pass, when said single photoelectron event instruction signal is non-significant.

20. The light measuring apparatus according to claim 18, wherein said light reducing means comprises:

a light reducing filter for receiving the pulsed light output from said pulsed light source, reducing the intensity of the light, and outputting the light toward the measurement object; and carrying means for locating said light reducing filter at a position where the light output from said pulsed light source passes, when said single photoelectron event instruction signal is significant, and locating said light reducing filter at a position where the light output from said pulsed light source does not pass, when said single photoelectron event instruction signal is non-significant.

21. The light measuring apparatus according to claim 3, further comprising an optical system to which the measurement-object light is incident and which makes the incident measurement-object light incident to a predetermined zone of said photoelectric conversion surface.

22. The light measuring apparatus according to claim 1, wherein said collecting means comprises:

a discriminator for receiving a current signal output from each said electron multiplier portion in accordance with each said electron multiplier portion and outputting a discrimination signal of photoelectron occurrence when a current value is at least a predetermined value, in said gate period; and recording means for recording event occurrence for each zone of said photoelectric conversion surface as regarding as an event a case wherein said discrimination signal becomes significant one or more times within said gate period; and wherein said estimating means estimates a mean value of photoelectrons emitted from each zone of said photoelectric conversion surface in said gate period, based on information of the event occurrence recorded in said recording means, thereby obtaining the intensity of the measurement-object light.

23. The light measuring apparatus according to claim 22, wherein said estimating means estimates said mean value by the maximum likelihood method.

24. The light measuring apparatus according to claim 22, wherein said estimating means estimates said mean value under such an assumption that a distribution of numbers of photoelectrons emitted from each zone of said photoelectric conversion surface is a poisson distribution.

25. The light measuring apparatus according to claim 22, further comprising a measurement control section for issuing a gate signal designating said gate period and for giving an instruction of activation of said estimating means.

26. The light measuring apparatus according to claim 22, further comprising:

a pulsed light source for outputting pulsed light to irradiate the measurement object and a generation timing signal of said pulsed light;

operation timing signal generating means for issuing a gate signal designating said gate period from the generation timing signal of said pulsed light;

a counter for counting a number of generation times of said pulsed light from the generation timing signal of said pulsed light; and a measurement control section for giving an instruction of activation of said estimating means.

27. The light measuring apparatus according to claim 22, further comprising a homogenizing optical system for homogenizing an intensity distribution on said photoelectric conversion surface, of the measurement-object light incident thereto.

28. The light measuring apparatus according to claim 22, further comprising a dividing optical system for receiving the measurement-object light, dividing the measurement-object light, and making each divided light incident to a corresponding zone of said photoelectric conversion surface.

29. The light measuring apparatus according to claim 1, wherein light incident thereto is separated and light of a wavelength selected is output toward said photodetection means.

* * * * *